(12) United States Patent
Purchase, Jr. et al.

(10) Patent No.: US 6,307,089 B2
(45) Date of Patent: Oct. 23, 2001

(54) BIPHENYL BUTYRIC ACIDS AND THEIR DERIVATIVES AS INHIBITORS OF MATRIX METALLOPROTEINASES

(75) Inventors: Claude Forsey Purchase, Jr., Ann Arbor; Bruce David Roth, Plymouth; Gerald Paul Schielke; Lary Craswell Walker, both of Ann Arbor; Andrew David White, Pinckney, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/736,802

(22) Filed: Dec. 14, 2000

Related U.S. Application Data

(62) Division of application No. 09/254,231, filed as application No. PCT/US97/14852 on Aug. 22, 1997, now Pat. No. 6,239,288.
(60) Provisional application No. 60/054,905, filed on Aug. 26, 1997, provisional application No. 60/027,138, filed on Oct. 2, 1996, and provisional application No. 60/025,814, filed on Sep. 4, 1996.

(51) Int. Cl.$^7$ .......................... C07C 69/76; C07C 68/95; C07C 59/40; C07C 59/74; A61K 31/15; A61K 31/192
(52) U.S. Cl. .......................... 560/51; 514/545; 514/568; 514/616; 560/59; 562/459; 562/468
(58) Field of Search ........................ 560/57, 59; 562/459, 562/468; 514/568, 545, 616

(56) References Cited

U.S. PATENT DOCUMENTS

| | | | |
|---|---|---|---|
| 3,182,061 | * | 5/1965 | Goldschmidt ..................... 562/459 X |
| 3,859,363 | * | 1/1975 | Teufel et al. ..................... 562/459 X |
| 3,997,589 | * | 12/1976 | Seeger et al. ..................... 562/459 X |
| 5,192,753 | | 3/1993 | McGeer et al ..................... 514/159 |
| 5,886,043 | * | 3/1999 | Kluender et al. ..................... 514/568 |
| 6,239,288 | * | 5/2001 | Purchase et al. ..................... 548/469 |

FOREIGN PATENT DOCUMENTS

| | | | |
|---|---|---|---|
| 2524463 | * | 10/1983 | (FR) ..................................... 562/459 |
| 72-03400 | * | 3/1971 | (NE) ..................................... 562/459 |
| WO/96/15096 | | 5/1996 | (WO) . |

OTHER PUBLICATIONS

Aisen P.S., "Anti–inflammatory therapy for Alzheimer's disease", *Neurobiology of Aging*, vol. 21, pp. 447–448 (2000).
Andersen, K. et al., "Do nonsteroidal anti–inflammatory drugs decrease the risk for Alzheimer's disease? The Rotterdam Study", *Neurology*, vol. 45, pp. 1441–1445 (Aug. 1995).
Andrews, H.J. et al., "A synthetic peptide metalloproteinase inhibitor, but not Timp, preventsthe breakdown of proteoglycan within articular cartlage in vitro", *Agents Actions*, vol. 37, pp. 147–154 (1992).
Armstrong, P.W. et al., "Structural remodeling in heart failure: gelatinase induction", *Can. J. Cardiol.*, vol. 10, No. 2, pp. 214–230 (Mar. 1994).
Bendeck, M. et al., "Smooth muscle cell migration and matrix metalloproteinase expression after arterial injury in the rat", *Circulation Research*, vol. 75, No. 3, pp. 539–545 (Sep. 1994).
Benelli, R. et al., "Inhibition of AIDS–Kaposi's Sarcoma Cell–Induced Endothelial Cell Invasion by TIMP–2 and a Synthetic Peptide from the Metalloproteinase Propeptide: Implications for an Anti–Angiogenic Therapy", *Oncology Research*, vol. 6, No. 6, pp. 251–257 (1994).
Breitner, J.C.S. et al., "Inverse assocation of anti–inflammatroy treatments and Alzheimer's disease: Inital results of a co–twin control study", *Neurology*, 44:227–232 (Feb. 1994).
Breitner, J.C.S. et al., "Delayed onset of Alzheimer's disease with nonsteroidal anti–inflammatory and histamine H2 blocking drugs", *Neurobiol. Aging*, vol. 165, No. 4, pp. 523–530 (1995).
Brown, S.I. et al., "Collagenolytic activity of alkali burned corneas", *Arch. Ophthalmol.*, vol. 81, pp. 370–373 (Mar. 1969).
Burns, F. et al., *Invest. Ophthalmol.*, vol. 30, No. 7, pp. 1569–1575 (Jul. 1989).
"The Canadian Study of Helath and Aging: Risk factors for Alzheimer's disease in Canada", *Neurology*, vol. 44, pp. 2073–2080 (Nov. 1994).
Child, R. et al., "Fenbufen, a New Anti–Inflammatory Analgesic: Synthesis and Structure–Activity Relationships of Analogs", *Journal of Pharmaceutical Science*, vol. 66, No. 4, pp. 466–476 (Apr. 1977).
Clark, R.K. et al., "Development of tissue damage, inflammation and resolution following stroke: an immunohistochemial and quantitative planimetric study", *Brain Research Bulletin*, vol. 31, pp. 565–572 (1993).
Davies, B. et al., et al., "A synthetic Matrix Metalloproteinase Inhibitor Decreases Tumor Burden and Prolongs Survival of Mice Bearing Human Ovarian Carcinoma Xenografts", *Cancer Reasearch*, vol. 53, pp. 2087–2091 (May 1, 1993).

(List continued on next page.)

*Primary Examiner*—Floyd D. Higel
(74) *Attorney, Agent, or Firm*—Merchant & Gould P.C.

(57) ABSTRACT

Biphenyl butyric acid compounds and derivatives are described as well as acid methods for the preparation and pharmaceutical compositions of same, which are useful as inhibitors of matrix metalloproteinases, particularly gelatinase A (72 kD gelatinase) and stromelysin-1 and for the treatment of multiple sclerosis, atherosclerotic plaque rupture, aortic aneurism, heart failure, restenosis, periodontal disease, corneal ulceration, treatment of burns, decubital ulcers, wound healing, cancer, inflammation, pain, arthritis, or other autoimmune or inflammatory disorders dependent upon tissue invasion by leukocytes or other activated migrating cells.

30 Claims, No Drawings-

OTHER PUBLICATIONS

DeClerck, Y. et al., "Inhibition of Invasion and Metastasis in Cells Transfected with an Inhibitor of Metalloproteinases", *Cancer Res.*, vol. 52, pp. 701–708 (Feb. 1, 1992).

Ellis, A.J. et al., "The Prevention of Collegen Breakdown in Bovine Nasal Cartliage by TIMP, TIMP-2 and a Low Molecular Weight Synthetic Inhibitor", *Biochemical and Biophysical Research Communications*, vol. 201, No. 1, pp. 94–101 (May 30, 1994).

Freije, José et al., *Journal of BiologicalChemistry*, vol. 269, No. 24, pp. 16766–16773 (1994).

Galis, Z. et al, "Increased expression of matrix metalloproteinases and matrix degrading activity in vulnerable regions of human atherosclerotic plaques", *J. Clin. Invest.*, vol. 94, pp. 2493–2503 (Dec. 1994).

Gendelamn, H. et al., "Macrophages/microglia and the pathoophysiology of CNS injuries in AIDS", *Journal of Leukocyte Biology*, vol. 56, pp. 387–388 (Sep. 1994).

Gijbels, K. et al., *J. Clin. Invest.*, vol. 94, pp. 2177–2182 (Dec. 1994).

Giulian D. et al., "Inflammatory glia mediate delayed neuronal damage after ischemia in the central nervous system", *Inflammatory Neurotoxins and Stroke/Supplement I Stroke*, vol. 24, No. 12, pp. 184–190 (Dec. 1993).

Hampel, H. et al, "Inflammatory and Immunological Mechanisms in Alzheimer's Disease", *DN&P*, vol. 8, No. 10, pp. 599–608 (Dec. 1995).

Henney A. et al., "Localization of stromelyssin gene expression in atherosclerotic plaques by in situ hybridization", *Proc. Nat'l. Acad. Sci.*, vol. 88, pp. 8154–8158 (Sep. 1991).

Lee, T. et al., "Impact of Left Ventricular Size on the Survival in Advanced Heart Failure", *Am. J. Cardiol.*, vol. 72, pp. 672–676 (Sep. 5, 1993).

Leigh P.N., "Pathogenic Mechanisms in Amyotrophic Lateral Sclerosis and Other Motor Neuron Disorders", *Neurodegenerative Diseases*, W.B. Saunders Company, Chapter 28, pp. 473–488 (1994).

Lucca, U. et al., "Nonsteroidal Antiinflammatory Drug Use in Alzheimer's Disease", *Society of Biological psychiatry*, vol. 36, pp. 854–866 (1994).

Mandybur T.I., et al. "Cerebral Amyoid Angiopathy With Granulomatous Antgiitis Ameliorated by Steroidi–Cytoxan Treatment", *Clin. Neuropharm.*, vol. 15, No. 3, pp. 241–247 (1992).

Martin R. et al., "Immunological Aspects of Demyelinating Diseases", *Annul Rev. Immunol.*, vol. 10, pp. 153–187 (1992).

Martin, R. et al., "Immunological Aspects of Experimental Allergic Encephalomyelitis and Multiple Sclerosis", *Critical Review in Clinical Laboratory Sciences*, vol. 32, No. 2, pp. 121–182 (1995).

McGeer, E., "Neurodegeneration and the Immune System", In: *Neurodegenerative Diseases*, W.B. Saunders, Chapter 18, pp. 277–300 (1994).

McGeer,P. et al., "Anti–inflammatory agents as a therapeutic approach to Alzheimer's disease", *Neurology*, vol. 42, pp. 447–449 (Feb., 1992).

McGeer, P. et al., Neuroimmune Mechanisms in Alzheimer Disease Pathogenesis, *Alzheimer Disease and Associated Disorders*, vol. 8, No. 3, pp. 149–158 (1994).

Melchiori, A. et al., "Inhibition of Tumor Cell Invasion by a Highly Conserved Peptide Sequence from the Matrix Metalloproteinase Enzyme Prosegment", *Cancer Res.*, vol. 52, pp. 2353–2356 (Apr. 15, 1992).

Monsky, W. et al., "Binding and Localization of $M_r$ 72,000 Matrix Metalloproteinase at Cell Surface Invadopodia", *Cancer Research*, vol. 53, pp. 3159–3164 (1993).

Overall, C.M. et al., "Demonstrations of tissue collagenase activity in vivo and its relationship to inflammation severity in human gingiva", *Journal of Periodontal Research*, vol. 22, pp. 81–88 (1987).

Patterson, P., "Cytokines in Alzheimer's disease and multiple sclerosis", *Current Opinion in Neurobiology*, vol. 5, pp. 642–646 (1995).

Pauly, R. et al., "Migration of Cultured Vascular Smooth Muscle Cells Through a Basement Membrane Barrier Requires Type IV Collagenase Activity and Is Inhibited by Cellular Differentiation", *Circulation Research*, vol. 75, No. 1, pp. 41–54 (Jul. 1994).

Reddy, H.K. et al., [Abstract] "Activated myocardial collagenase in idiopathic dilated cardiomyopathy: A marker of dilation and remodeling", *Clinical Research*, vol. 41, No. 3, p. 660A (1993).

Rich, J.B. et al., "Nonsteroidal anti–inflammatory drugs in Alzheimer's disease", *Neurology*, vol. 45, pp. 51–55 (1995).

Rogers, J. et al., "Inflammation and Alzheimer's Disease Pathogenesis", *Neurobiology of Aging*, vol. 17, No. 5, pp. 681–686 (1996).

Romanic, A. et al., "The Induction of 72–kDa Gelatinase in T Cells upon Adhesion to Endothelial Cells is VCAM–1 Dependent", *The Journal of Cell Biology*, vol. 125, pp. 1165–1178 (Jun. 1994).

Rotherwell, N.J. et al., "Involvement of Cytokines in Acute Neurodegeneration in the CNS", *Neuroscience and Biobehavioral Reviews*, vol. 17, pp. 217–227 (1993).

Saarialho–Kere, U. et al., "Distinct Populations of Basal Keratinocytes Express Stromelysin–1 and Stromelysin–2 in Chronic Wounds", *J. Clin. Invest.*, vol. 94, pp. 79–88 (Jul. 1994).

Sabbah, H. et al, "Left ventricular shape changes during the course of evolving heart failure", *The American Physiological Society*, vol. 263, pp. H266–H270 (1992).

Sato, H. et al, "A matrix metalloproteinase expressed on the surface of invasive tumor cells", *Nature*, vol. 370, pp. 61–65 (Jul. 7, 1994).

Strongin, A. et al., "Plasma Membrane–dependent Activation of the 72–kDa Type IV Collagenase Is Prevented by Complex Formation with TIMP–2", *The Journal of Biological Chemistry* vol. 268, No. 19, pp. 14033–14039 (Jul. 5, 1993).

Taraboletti, G. et al., "Inhibition of Angiogenesis and Murine Hemangioma Growth by Batimastat, a Synthetic Inhibitor of Matrix Metalloproteinases", *Journal of the National Cancer Institute*, vol. 87, No. 4, pp. 293–298 (Feb. 15, 1995).

Uitto, V.J. et al., "Collagenase and neutral metalloproteinase activity in extracts from inflamed human gingival", *Journal of Periodontal Research*, vol. 16, pp. 417–424 (1981).

Vine, N. et al., "Metalloproteinases in degenerative aortic diseases", *Clinical Science*, vol. 81, pp. 233–239 (1991).

Walakovits, L. et al., "Detection of Stromelysin and Collagenase in Synovial Fluid from Patients with Rheumatoid Arthritis and Posttraumatic Knee Injury", *Arthritis and Rheumatism,* vol. 35, No. 1, pp. 35–42 (Jan. 1992).

Woessner Jr., J. "Matrixi metalloproteinases and their inhibitors in connective tissue remodeling", *The FASEB Journal,* vol. 5, pp. 2145–2154 (May 1991).

Zafarullah, M. et al., "Elevated Metalloproteinases and Tissue Inhibitor of Metalloproteinase mRNA in Human Osteoarthritic Synovia", *The Journal of Rheumatology,* vol. 20, No. 4, pp. 693–697 (1993).

\* cited by examiner

BIPHENYL BUTYRIC ACIDS AND THEIR DERIVATIVES AS INHIBITORS OF MATRIX METALLOPROTEINASES

This application is a divisional of application Ser. No. 09/254,231, filed Mar. 2, 1999, now U.S. Pat. No. 6,239,288, which is a § 371 of PCT/US97/14852 of Aug. 22, 1997, which claims priority to provisional applications: 60/054,905 of Aug. 26, 1997, 60/027,138 of Oct. 2, 1996, and 60/025,814 of Sep. 4, 1996, which application(s) are incorporated hereby by reference.

BACKGROUND OF THE INVENTION

The present invention relates to novel biphenyl butyric acid compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (72 kDa gelatinase) and stromelysin-1. More particularly, the novel compounds of the present invention are useful in the treatment of atherosclerotic plaque rupture, aortic aneurism, heart failure, restenosis, periodontal disease, corneal ulceration, treatment of burns, decubital ulcers, wound repair, cancer, inflammation, pain, arthritis, multiple sclerosis, and other autoimmune or inflammatory disorders dependent on the tissue invasion of leukocytes or other activated migrating cells. Additionally, the compounds of the present invention are useful in the treatment of acute and chronic neurodegenerative disorders including stroke, head trauma, spinal cord injury, Alzheimer's disease, amyotrophic lateral sclerosis, cerabral amyloid anigopathy, AIDS, Parkinson's disease, Huntington's disease, prion diseases, myasthenia gravis, and Duchenne's muscular dystrophy.

Gelatinase A and stromelysin-1 are members of the matrix metalloproteinase (MMP) family (Woessner J. F., *FASEB J.*, 1991;5:2145–2154). Other members include fibroblast collagenase, neutrophil collagenase, gelatinase B (92 kDa gelatinase), stromelysin-2, stromelysin-3, matrilysin, collagebase 3 (Freije J. M., Diez-Itza I., Balbin M., Sanchez L. M., Blasco R., Tolivia J., and Lopez-Otin C., *J. Biol. Chem.*, 1994;269:16766–16773), and the membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is a focal point for inhibitor design. The modification of substrates by introducing chelating groups has generated potent inhibitors such as peptide hydroxymates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of an atherosclerotic plaque in the most common event initiating coronary thrombosis. Destablization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galis Z. S., Sukhova G. K., Lark M. W., and Libby P., "Increased expression of matrix metalloproteinases and matrix degrading activity in vulnerable regions of human atherosclerotic plaques", *J. Clin. Invest.* 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l Acad. Sci.*, 1991;88:8154–8158).

Inhibitors of matrix metalloproteinases will have utility in treating degenerative aortic disease associated with thinning of the medial aortic wall. Increased levels of the proteloytic activities of MMPs have been identified in patients with aortic aneurisms and aoritic stenosis (Vine N. and Powell J. T., "Metalloproteinases in degenerative aortic diseases", *Clin. Sci.*, 1991;81:233–239).

Heart failure arises from a number of diverse etiologies, but a common characteristic is cardiac dilation, which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.*, 1993;72:672–676).

This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy", *Clin. Res.*, 1993;41:660A; Tyagi S. C., Reddy H. K., Voelker D., Tjara I. E., and Weber K. T., "Myocardial collagenase in failing human heart", *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction ", *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure ", *Am. J. Physiol.*, 1992;263:H266–270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat", *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation", *Circulation Research*, 1994;75:41–54).

Collagenase and stromelysin activities have been demonstrated in fibroblasts isolated from inflamed gingiva (Utto V. J., Applegreen R., and Robinson P. J., "Collagenase and neutral metalloproteinase activity in extracts from inflamed human gingiva", *J. Periodontal Res.*, 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva", *J. Periodontal Res.*, 1987;22:81–88). Proteolytic degradation of extracellular matrix has been observed in corneal ulceration following alkali burns (Brown S. I., Weller C. A., and Wasserman H. E., "Collagenolytic activity of alkali burned corneas", *Arch. Ophthalmol.*, 1969;81:370–373). Thiol-containing peptides inhibit the collagenase isolated from alkali-burned rabbit corneas (Burns F. R., Stack M. S., Gray R. D., and Paterson C. A., *Invest. Ophthalmol.*, 1989;30:1569–1575).

Stromelysin is produced by basal keratinocytes in a variety of chronic ulcers (Saarialho-Kere U. K., Ulpu K., Pentland A. P., Birkedal-Hansen H., Parks, W. O., and Welgus H. G., "Distinct Populations of Basal Keratinocytes Express Stromelysin-1 and Stromelysin-2 in Chronic Wounds", *J. Clin. Invest.*, 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies, et al., (*Cancer Res.*, 1993;53:2087–2091) reported that a peptide hydroxymate, BB-94, decreased the tumor burned and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.*, 1992;52:2353–2356). The natural tissue inhibitor of metalloproteinase-2 (TIMP-2) also showed blockage of tumor cell invasion in in vitro models (DeClerck Y. Al., Perez N., Shimada H., Boone T. C., Langley K. E., and Taylor S. M., *Cancer Res.*, 1992;52:701–708). Studies of human cancers have shown that gelatinase A is activated on the invasive tumor cell surface (Strongin A. Y., Marmer B. L., Grant G. A., and Goldberg G. I., *J. Biol. Chem.*, 1993;268:14033–14039) and is retained there through interaction with a receptor-like molecule (Monsky W. L., Kelly T., Lin C.-Y., Yeh Y., Stetler-Stevenson W. G., Mueller S. C., and Chen W. -T., *Cancer Res.*, 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute*, 1995;87:293 and Benelli R., Adatia R., Ensoli B., Stetler-Stevenson W. G., Santi L., and Albini A., *Oncology Research*, 1994;6:251–257).

Several investigators have demonstrated consistent elevation of stromelysin and collagenase in synovial fluids from osteo- and rheumatoid arthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury", *Arthritis Rheum.*, 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia", *J. Rheumatol.*, 1993;20:693–697). TIMP-1 and TIMP-2 prevented the formation of collagen fragments, but not proteoglycan fragments in both the bovine nasal, and pig articular cartilage models for arthritis, while a synthetic peptide hydroxamate could prevent the formation of both fragments (Andrews H. J., Plumpton T. A., Harper G. P., and Cawston T. E., *Agents Actions*, 1992;37:147–154; Ellis A. J., Curry V. A., Powell E. K., and Cawston T. E., *Biochem. Biophys. Res. Commun.*, 1994;201:94–101).

Gijbels et al., (*J. Clin. Invest.*, 1994;94:2177–2182) recently described a peptide hydroxamate, GM6001, that suppressed the development or reversed the clinical expression of experimental autoimmune encephalomyelitis (EAE) in a dose dependent manner, suggesting the use of MMP inhibitors in the treatment of autoimmune inflammatory disorders such as multiple sclerosis.

A recent study of Madri has elucidated the role of gelatinase A in the extravasation of T-cells from the blood stream during inflammation (Ramanic A. M., and Madri J. A., "The Induction of 72-kDA Gelatinase in T Cells upon Adhesion to Endothelial Cells is VCAM-1 Dependent", *J. Cell Biology*, 1994;125:1165–1178). This transmigration past the endothelial cell layer is coordinated with the induction of gelatinase A and is mediated by binding to the vascular cell adhesion molecule-1 (VCAM-1). Once the barrier is compromised, ederma and inflammation are produced in the CNS. Also, leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

Neuroinflammatory mechanisms are implicated in a broad range of acute and chronic neurodegenerative disorders, including stroke, head trauma, multiple sclerosis, and Alzheimer's disease, to name a few (McGeer E. G., and McGeer P. L., "Neurodegeneration and the immune system", In: Calne D. B., ed. Neurodegenerative Diseases, W. B. Saunders, 1994:277–300). Other disorders that may involve neuroinflammatory mechanisms include amyotrophic lateral sclerosis (Leigh P. N., "Pathogenic mechanisms in amyotrophic lateral sclerosis and other motor neuron disorders", In: Calne D. B., ed., Neurodegenerative Diseases, W. B. Saunders, 1994:473–88), cerebral amyloid angiopathy (Mandybur T. I., and Balko G., "Cerebral amyloid angiopathy with granulomatous angiitis ameliorated by steroid-cytoxan treatment", *Clin. Neuropharm.*, 1992;15:241–7), AIDS (Gendelman H. E. and Tardieu M., "Macrophages/microglia and the pathophysiology of CNS injuries in AIDS", *J. Leukocyte Biol.*, 1994;56:387–8), Parkinson's disease, Huntingdon's disease, prion diseases, and certain disorders involving the peripheral nervous system, such as myasthenia gravis and Duchenne's muscular dystrophy. Neuroinflammation, which occurs in response to brain injury or autoimmune disorders, has been shown to cause destruction of healthy tissue (Martin R., MacFarland H. F., and McFarlin D. E., "Immunological aspects of demyelinating diseases", *annul Rev. Immunol.*, 1992;10:153–87; Clark R. K., Lee E. V., Fish C. J., et al., "Development of tissue damage, inflammation and resolution following stroke: an immunehistochemical and quantitive planimetric study", *Brain Res. Bull.,* 1993;31:565–72; Giulian D. and Vaca K., "Inflammatory glia mediate delayed neuronal damage after ischemia in the central nervous system", *Stroke,* 1993;24(Suppl 12):184–90; Patterson P. H., "Cytokines in Alzheimer's disease and multiple sclerosis", *Curr. Opinion Neurobiol,* 1995;5:642–6; McGeer P. L., Rogers J., and McGeer E. G., "Neuroimmune mechanisms in Alzheimer disease pathogenesis", *Alzheimer Dis. Assoc. Disorders,* 1994;8:149–58; Martin R. and McFarland H. F., "Immunological aspects of experimental allergic encephalomyelitis and multiple sclerosis", *Crit. Rev. Clin. Lab. Scie.,* 1995;32:121–82; Rogers J., Webster S., Lue L. F., et al., "Inflammation and Alzheimer's disease pathogenesis", In: *Neurobiology of Aging,* 1996;17:681–686; Rothwell N. J. and Relton J. K., "Involvement of cytokines in acute neurodegeneration in the CNS", *Neurosci. Biobehav. Rev.,* 1993;17:217–27). The pathological profiles and clinical courses of these disorders differ widely, but they all have in common the participation of immune/inflammatory elements in the disease process. In particular, many neurodegenerative disorders are characterized by large numbers of reactive microglia in postmortem brain samples, indicative of an active inflammatory process (McGeer E. G., and McGeer P. L., supra., 1994).

Increasing attention is being directed toward inflammatory mechanisms in Alzheimer's disease. Several lines of evidence support the involvement of neuroinflammation in Alzheimer's disease: 1) There is a significant increase in inflammatory markers in the Alzheimer brain, including acute phase reactants, cytokines, complement proteins, and MHC molecules (McGeer, et al., supra., 1994; Rogers, et al., supra.); 2) There is evidence that β-amyloid induces neuordegenerative changes primarily through interactions with inflammatory molecules, and that inflammation alone is sufficient to induce neurodengeneration (Rogers et al., supra); and 3) Growing epidemiological data indicate that antiinflammatory therapy can delay the onset and slow the progression of Alzheimer's disease (McGeer P. L., and Rogers J., "Anti-inflammatory agents as a therapeutic approach to Alzheimer's disease", *Neurology,* 1992;42:447–9; Canadian Study of Health and Aging, "Risk factors for Alzheimer's disease in Canada", *Neurology,* 1994;44:2073–80; Lucca U., Tertamanti M., Forloni G., and Spagnoli A., "Nonssteroidal antiinflammatory drug use in Alzeheimer's disease", *Biol. Psychiatry,* 1994;36:854–66; Hampel H. and Muller N., "Inflammatory and immunological mechanisms in Alzheimer's disease", *DN&P,* 1995;8:599–608; Breitner J. C. S., Gau B. A., Welsh K. A., et al., "Inverse association of anti-inflammatory treatments and Alzheimer's disease: Initial results of a co-twin control study", *Neurology,* 1994;44:227–32; Breitner J. C. S., Welsh K. A., Helms M. J., et al., "Delayed onset of Alzheimer's disease with nonsteroidal anti-inflammatory and histamine H2 blocking drugs", *Neurobiol. Aging,* 1995;16:523–30; Andersen K., Launer L. J., Ott A., Hoes A. W., Breteler M. M. B., and Hofman A., "Do nonsteroidal anti-inflammatory drugs decrease the risk for Alzheimer's disease! The Rotterdam Study", *Neurology,* 1995;45:1441–5; Rich J. B., Rasmusson D. X., Folstein M. F., et al., "Nonsteroidal anti-inflammatory drugs in Alzheimer's disease", *Neurology,* 1995;45:51–5; Aisen P. S., "Anti-inflammatory therapy for Alzheimer's disease", *Dementia,* 1995;9:173–82; Rogers, et al., supra). Chronic use of nonsteroidal antiinflammatory drugs (NSAIDs), most commonly for the treatment of rheumatoid arthritis, decreases the probability of developing Alzheimer's disease, and there is reason to believe that other antiinflammatory agents may also be effective, although direct evidence for the efficacy of such treatments is lacking (Hamper and Meller, supra., 1995). Furthermore, virtually all of the currently available compounds, which include corticosteroids, NSAIDs, antimalarial drugs, and colchicine, have serious drawbacks that make them undesirable in the treatment of chronic disorders. Glucocorticoids, which are in wide clinical use as antiinflammatory/immunosuppressive drugs, can be directly neurotoxic and also are toxic to systemic organs at moderate to high doses. NSAIDs have gastrointestinal and renal side effects that obviate long-term use in most people, and few of them cross the blood-brain barrier in significant amounts. The toxic properties of chloroquine compounds and colchicine also are well known. An antiinflammatory drug that is well-tolerated by patients and that crosses the blood-brain barrier has significant advantages for the treatment of acute and chronic degenerative diseases of the central nervous system.

We have identified a series of biphenyl butyric acid compounds and derivatives that are inhibitors of matrix metalloproteinases, particularly stromelysin-1 and gelatinase A, and thus useful as agents for the treatment of multiple sclerosis, atherosclerotic plaque rupture, restenosis, aortic aneurism, heart failure, periodontal disease, corneal ulceration, treatment of burns, decubital ulcers, wound repair, cancer, inflammation, pain, arthritis, or other autoimmune or inflammatory diseases dependent upon tissue invasive by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's diseases, prion diseases, myasthenic gravis, and Duchenne's muscular dystrophy.

SUMMARY OF THE INVENTION

Accordingly, a first aspect of the present invention is a compound of Formula I

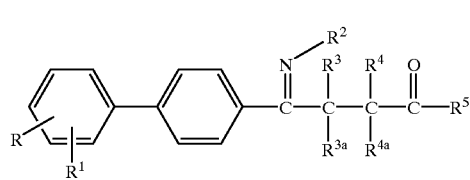

wherein R and $R^1$ are the same or different and are hydrogen.

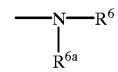

defined above for $R^6$,

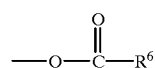

wherein R⁶ is as defined above,

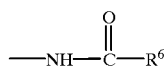

wherein R⁶ is as defined above,

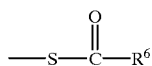

wherein R⁶ is as defined above,
—SR⁶ wherein R⁶ is as defined above,

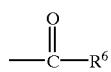

wherein R⁶ is as defined above,
—CH₂—OR⁶ wherein R⁶ is as defined above,

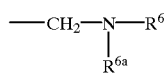

wherein R⁶ and R⁶ᵃ are the same or different and are as defined above for R⁶,

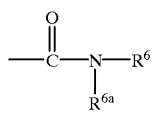

wherein R⁶ and R⁶ᵃ are the same or different and are as defined above for R⁶,

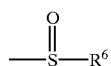

wherein R⁶ is as defined above,

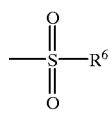

wherein R⁶ is as defined above,
cycloalkyl, or
heteroaryl, with the proviso that R and R¹ are not both hydrogen;
R² is OR⁶ wherein R⁶ is as defined above, or

wherein R⁶ and R⁶ᵃ are the same or different and are as defined above for R⁶;
R³, R³ᵃ, R⁴, and R⁴ᵃ are the same or different and are hydrogen,
fluorine,
alkyl,
—(CH₂)ₙ-aryl wherein n is an integer from 1 to 6,
—(CH₂)ₙ-heteroaryl wherein n is as defined above,
—(CH₂)ₙ-cycloalkyl wherein n is as defined above,
—(CH₂)ₚ—X—(CH₂)_q-aryl wherein X is O, S, SO, SO₂, or NH, and p and q are each zero or an integer of 1 to 6, and the sum or p+q is not greater than six,
—(Ch₂)ₚ—X—(CH₂)_q-heteroaryl wherein X, p, and q are as defined above, or
—(CH₂)ₙ-R⁷ wherein R⁷ is
N-phthalimido,
N-2,3-naphthylimido,
—OR⁶ wherein R⁶ is as defined above,

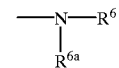

wherein R⁶ and R⁶ᵃ are the same or different and are as defined above for R⁶,
—SR⁶ wherein R⁶ is as defined above,

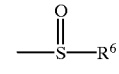

wherein R⁶ is as defined above,

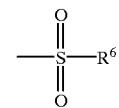

wherein R⁶ is as defined above,

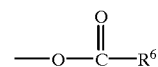

wherein R⁶ is as defined above,

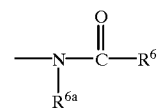

wherein R⁶ and R⁶ᵃ are the same or different and are as defined above for R⁶,

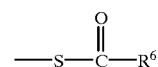

wherein R⁶ is as defined above,

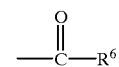

wherein R⁶ is as defined above,

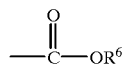

wherein R⁶ is as defined above, or

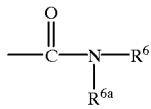

wherein R⁶ and R⁶ᵃ are the same or different and are as defined above for R⁶, and n is as defined above;

R⁵ is OH, SH, or OR⁵ᵃ wherein R⁵ᵃ is alkyl, arylalkyl, cycloalkyl, or acyloxymethyl; with the proviso that R³, R³ᵃ, R⁴, and R⁴ᵃ are hydrogen or at least one of R³, R³ᵃ, R⁴, or R⁴ᵃ is fluorine;

and corresponding isomers thereof; or a pharmaceutically acceptable salt thereof.

A second aspect of the present invention is a compound of Formula II

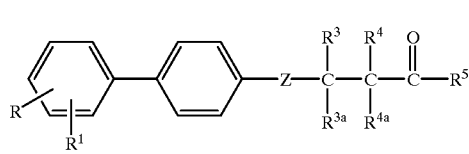

II wherein R and R¹ are the same or different and are hydrogen,
alkyl,
halogen,
nitro,
cyano,
trifluoromethyl,
OCF₃,
OCF₂H,
OCH₂F,
—OR⁶ wherein R⁶ is hydrogen,
alkyl,
aryl,
arylalkyl,
heteroaryl, or
cycloalkyl,

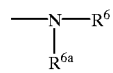

wherein R⁶ and R⁶ᵃ are the same or different and are as defined above for R⁶,

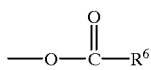

wherein R⁶ is as defined above,

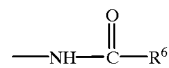

wherein R⁶ is as defined above,

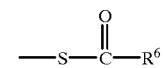

wherein R⁶ is as defined above,
—SR⁶ wherein R⁶ is as defined above,

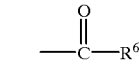

wherein R⁶ is as defined above,
—CH₂—OR⁶ wherein R⁶ is as defined above,

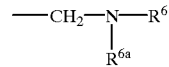

wherein R⁶ and R⁶ᵃ are the same or different and are as defined above for R⁶,

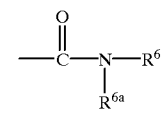

wherein R⁶ and R⁶ᵃ are the same or different and are as defined above for R⁶,

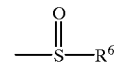

wherein R⁶ is as defined above,

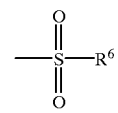

wherein R⁶ is as defined above,
cycloalkyl, or
heteroaryl;

Z is 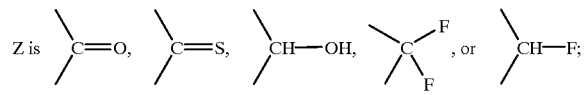

R³, R³ᵃ, R⁴, and R⁴ᵃ are the same or different and are
hydrogen,
fluorine,
alkyl,
—(CH₂)ₙ-aryl wherein n is an integer from 1 to 6, —(CH$_2$)$_n$-heteroaryl wherein n is as defined above, —(CH$_2$)$_n$-cycloalkyl wherein n is as defined above, —(CH$_2$)$_p$—X—(CH$_2$)$_q$-aryl wherein X is O, S, SO, SO$_2$, or NH, and p and q are each zero or an integer of 1 to 6, and the sum or p+q is not greater than six, —(CH$_2$)$_p$—X—(CH$_2$)$_q$-heteroaryl wherein X, p, and q are as defined above, or —(CH$_2$)$_n$-R$^7$ wherein R$^7$ is N-phthalimido, N-2,3-naphthylimido, —OR$^6$ wherein R$^6$ is as defined above,

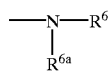

wherein R$^6$ and R$^{6a}$ are the same or different and are as defined above for R$^6$, —SR$^6$ wherein R$^6$ is as defined above,

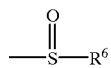

wherein R$^6$ is as defined above,

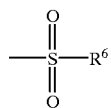

wherein R$^6$ is as defined above,

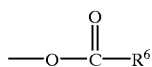

wherein R$^6$ is as defined above,

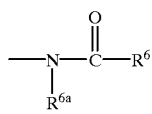

wherein R$^6$ and R$^{6a}$ are the same or different and are as defined above for R$^6$,

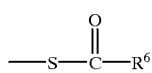

wherein R$^6$ is as defined above,

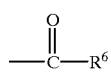

wherein R$^6$ is as defined above,

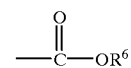

wherein R$^6$ is as defined above, or

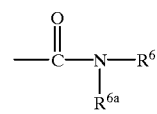

wherein R$^6$ and R$^{6a}$ are the same or different and are as defined above for R$^6$, and n is as defined above;

R$^5$ is OH, SH, or OR$^{5a}$ wherein R$^{5a}$ is alkyl, arylalkyl, cycloalkyl, or acyloxymethyl;

with the proviso that at least one of R$^3$, R$^{3a}$, R$^4$, or R$^{4a}$ is fluorine; and corresponding isomers thereof; or a pharmaceutically acceptable salt thereof.

As matrix metalloproteinase inhibitors, the compounds of Formula I and Formula II are useful as agents for the treatment of multiple sclerosis. They are also useful as agents for the treatment of atherosclerotic plaque rupture, aortic aneurism, heart failure, restenosis, periodontal disease, corneal ulceration, treatment of burns, decubital ulcers, wound repair, cancer metastasis, tumor angiogenesis, inflammation, pain, arthritis, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

A still further embodiment of the present invention is a pharmaceutical composition for administering an effective amount of a compound of Formula I or Formula II in unit dosage form in the treatment methods mentioned above. Finally, the present invention is directed to methods for production of compounds of Formula I.

DETAILED DESCRIPTION OF THE INVENTION

In the compounds of Formula I and Formula II, the term "alkyl" means a straight or branched hydrocarbon radical having from 1 to 8 carbon atoms and includes, for example, methyl, ethyl, n-propyl, isopropyl, n-butyl, sec-butyl, isobuty, tert-butyl, n-pentyl, n-hexyl, n-heptyl, n-octyl, and the like.

"Alkkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, SO$_3$OH, CHO,

as defined above for alkyl,

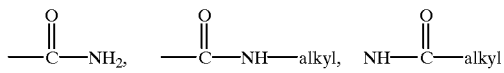

as defined above for alkyl,

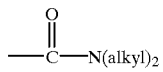

as defined above for alkyl, —(CH$_2$)$_n$2—NH$_2$ wherein n$^2$ is an integer of 1 to 5, —(CH$_2$)$_n$2—NH-alkyl as defined above for alkyl and n$^2$, —CH$_2$)$_n$2-N(alkyl)$_2$ as defined above for alkyl and n$^2$,

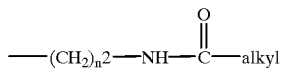

as defined above for alkyl, and n$^2$ and

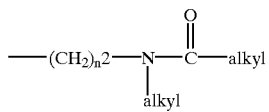

as defined above for alkyl and n$^2$.

The term "arylalkyl" means an aromatic radical attached to an alkyl radical wherein aryl and alkyl are as defined above for example benzyl, phenylethyl, 3-phenylpropyl, (4-chlorophenyl)methyl, and the like.

The term "acyloxymethyl" means a group of the formula

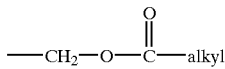

wherein alkyl is as defined above.

The term "heteroaryl" means a heteroaromatic radical and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl.

"Halogen" is fluorine, chlorine, bromine, or iodine.

"Alkali metal" is a metal in Group 1A of the periodic table and includes, for example, lithium, sodium, potassium, and the like.

Some of the compounds of Formula I and Formula II wherein R$^5$ is OH are capable of further forming pharmaceutically acceptable carboxylic esters which are suitable as prodrugs. All of these carboxylic esters are within the scope of the present invention.

Pharmaceutically acceptable carboxylic esters of compounds of Formula I and Formula II include alkyl, cycloalkyl, arylalkyl, or acyloxymethyy esters.

The alkyl, cycloalkyl, and arylalkyl carboxylic esters of compounds of Formula I and Formula II can be prepared by methods known to one skilled in the art. For example, the corresponding carboxylic acids can be allowed to react directly with a suitable alcohol in the presence of a suitable acid catalyst to give the carboxylic esters. Alternatively, the carboxylic acids can be allowed to react with one of a number of suitable activating agents, which are known to one skilled in the art, followed by reaction with a suitable alcohol to give the carboxylic esters. Additionally for the 4-hydroxyimino-butyric acids of the present invention, the carboxylic acids can be allowed to cyclo-dehydrate using one of a number of methods known to one skilled in the art to give a cyclic a 4,5-dihydro-6-oxo-6H-1,2-oxazine intermediate, which can be allowed to react with a suitable alcohol optionally in the presence of a suitable acid or base catalyst to give the carboxylic esters.

The acyloxymethyl esters of compounds of Formula I and Formula II can be prepared by methods known to one skilled in the art. For example, the corresponding carboxylic acids can be allowed to react first with a suitable base to give the carboxylate anion, followed by reaction with a carboxylic halomethyl ester, which can be obtained from commercial suppliers or prepared by methods known to one skilled in the art, optionally in the presence of a suitable agent to activate the carboxylic halomethyl ester, which are known to one skilled in the art, to give the acyloxymethyl esters.

Some of the compounds of Formula I and Formula II are capable of further forming both pharmaceutically acceptable acid addition and/or base salts. All of these forms are within the scope of the present invention.

Pharmaceutically acceptable acid addition salts of the compounds of Formula I and Formula II include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenefulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," J. of Pharma. Sci., 1977;66:1).

The acid addition salts of said basic compounds are prepared by contacting the free base with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma Sci.,* 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

In the first embodiment of the invention, a preferred compound of Formula I is one wherein $R^2$ is $OR^6$.

In the first embodiment of the invention, a more preferred compound of Formula I is one wherein $R^2$ is $OCH_3$.

In the first embodiment of the invention, a most preferred compound of Formula I is one wherein $R^2$ is OH, and $R^3, R^{3a}, R^4$, and $R^{4a}$ are hydrogen.

In the first embodiment of the invention, another more preferred compound of Formula I is one wherein $R^2$ is OH, and at least one of $R^3, R^{3a}, R^4$, and $R^{4a}$ is fluorine.

Particularly valuable in the first embodiment of the invention is a compound selected from the group consisting of:
4-(4'-Chloro-biphenyl-4-yl)-4-hydroxyimino-butyric acid;
4-(4'-Bromo-biphenyl-4-yl)-4-hydroxyimino-butyric acid;
4-(4'-Chloro-biphenyl-4-yl)-4-(dimethylhydrazono)-butyric acid;
4-(4'-Fluoro-biphenyl-4-yl)-4-hydroxyimino-butyric acid;
4-(4'-Bromo-2'-fluoro-biphenyl-4-yl)-4-hydroxyimino-butyric acid;
4-(2',4'-Dichloro-biphenyl-4-yl)-4-hydroxyimino-butyric acid;
4-(2',4'-Difluoro-biphenyl-4-yl)-4-hydroxyimino-butyric acid;
(±)-4-(4'-Chloro-biphenyl-4-yl)-4-hydroxyimino-2-fluoro-2-(3-phenylpropyl)-butyric acid;
(±)-4-(4'-Chloro-biphenyl-4-yl)-4-hydroxyimino-2-fluoro-2-(2-phenylethyl)-butyric acid;
(±)-4-(4'-Chloro-biphenyl-4-yl)-4-hydroxyimino-2-fluoro-2-(3-phthalimidopropyl)-butyric acid;
(±)-4-(4'-Chloro-biphenyl-4-yl)-4-hydroxyimino-2-fluoro-2-(phenylthiomethyl)-butyric acid;
4-(4'-Chloro-2'-fluoro-biphenyl-4-yl)-4-hydroxyimino-butyric acid;
4-Hydroxyimino-4-(4'-trifluoromethyl-biphenyl-4-yl)-butyric acid;
4-(4'-Chloro-biphenyl-4-yl)-4-methoxyimino-butyric acid;
(±)-4-(4'-Chloro-biphenyl-4-yl)-2-fluoro-2-[2-(1,3-dioxo-1,3-dihydro-isoindol-2-yl)-ethyl]-4-hydroxyimino-butyric acid;
(±)-4-(4'-Chloro-biphenyl-4-yl)-4-hydroxyimino-2-fluoro-2-(1H-indol-3-yl)methyl-butyric acid;
(±)-4-(4'-Chloro-biphenyl-4-yl)-4-hydroxyimino-2-fluoro-2-methyl-butyric acid;
(±)-2-[2-(4'-Chloro-biphenyl-4-yl)-2-hydroxyiminoethyl]-2-fluoro-6-phenyl-hexanoic acid;
(±)-4-(4'-Chloro-biphenyl-4-yl)-2-fluoro-2-[2-(1,3-dioxo-1,3-dihydrobenzo[F]isoindol-2-yl)-ethyl]-4-hydroxyimino-butyric acid;
(±)-2-[2-(4'-Chloro-biphenyl-4-yl)-2-hydroxyimino-ethyl]-6-(1,3-dioxo-1,3-dihydro-isoindol-2-yl)-2-fluoro-hexanoic acid;
(±)-4-(4'-Chloro-biphenyl-4-yl)-4-hydroxyimino-2-fluoro-2-[2-(phenylethylcarbamoyl)-ethyl]-butyric acid;
4-(4'-Chloro-biphenyl-4-yl)-3,3-difluoro-4-hydroxyimino-butyric acid;
(±)-4-(4'-Chloro-biphenyl-4-yl)-3,3-dimethyl-2-fluoro-4-hydroxyimino-butyric acid;
(±)-4-(4'-Chloro-biphenyl-4-yl)-2,2-dimethyl-3-fluoro-4-hydroxyimino-butyric acid;
4-(4'-Chloro-biphenyl-4-yl)-2,2-difluoro-4-hydroxyimino-butyric acid;
4-(4'-Chloro-biphenyl-4-yl)-2,2,3,3-tetrafluoro-4-hydroxyimino-butyric acid;
4-(4'-Chloro-biphenyl-4-yl)-4-methoxyimino-butyric acid, sodium salt;
4-(2'-Fluoro-biphenyl-4-yl)-4-hydroxyimino-butyric acid;
4-Hydroxyimino-4-(4'-methyl-biphenyl-4-yl)-butyric acid;
4-Hydroxyimino-4-(4'-methoxy-biphenyl-4-yl)-butyric acid;
4-(4'-Cyano-biphenyl-4-yl)-4-hydroxyimino-butyric acid;
4-(3'-Fluoro-biphenyl-4-yl)-4-hydroxyimino-butyric acid;
4-Hydroxyimino-4-(4'-methylsulfanyl-biphenyl-4-yl)-butyric acid;
4-(4'-Chloro-biphenyl-4-yl)-4-hydroxyimino-butyric acid, sodium salt monohydrate;
4-(4'-Chloro-biphenyl-4-yl)-4-hydroxyimino-butyric acid, hemi calcium salt;
4-(4'-Chloro-biphenyl-4-yl)-4-hydroxyimino-butyric acid, procaine salt;
4-(4'-Chloro-biphenyl-4-yl)-4-hydroxyimino-butyric acid, hemi magnesium salt, dihydrate;
4-(4'-tert-Butyl-biphenyl-4-yl)-4-hydroxyimino-butyric acid;
4-(3',4'-Dichloro-biphenyl-4-yl)-4-hydroxyimino-butyric acid; and
4-(4'-Chloro-biphenyl-4-yl)-4-hydroxyimino-butyric acid, 2,2-dimethylpropionyloxymethyl ester;
and corresponding isomers thereof; or a pharmaceutically acceptable salt thereof.

Most particularly valuable in the first embodiment of the invention is 4-(4'-chloro-biphenyl-4-yl)-4-hydroxyimino-butyric acid; and corresponding isomers thereof; or a pharmaceutically acceptable salt thereof.

In the second embodiment of the invention, a preferred compound of Formula II is one wherein Z is

and

R$^3$ and R$^{3a}$ are fluorine.

In another second embodiment of the invention, a preferred compound of Formula II is one wherein Z is

and

R$^4$ and R$^{4a}$ are fluorine.

In a second embodiment of the invention, a more preferred compound of Formula II is one wherein Z is

and

R$^3$ is fluorine.

In a second embodiment of the invention, another more preferred compound of Formula II is one wherein Z is

and

R$^4$ is fluorine.

In another second embodiment of the invention, a preferred compound of Formula II is one wherein Z is 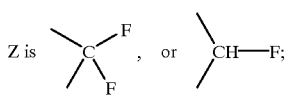

and

R$^3$ and R$^{3a}$ are fluorine.

In another second embodiment of the invention, a preferred compound of Formula II is one wherein Z is 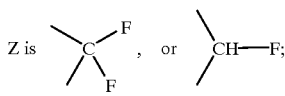

and

R$^4$ and R$^{4a}$ are fluorine.

In another second embodiment of the invention, a preferred compound of Formula II is one wherein Z is 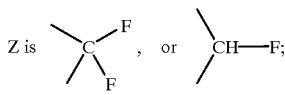

and

R$^3$ is fluorine.

In another second embodiment of the invention, a preferred compound of Formula II is one wherein Z is 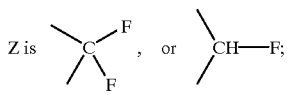

and

R$^4$ is fluorine.

Particularly valuable in the second embodiment of the invention is a compound selected from the group consisting of:

(±)-4-(4'-Chloro-biphenyl-4-yl)-4-hydroxy-butyric acid; and (±)-4-(4'-Chloro-biphenyl-4-yl)-3-fluoro-4-oxo-butyric acid;

and corresponding isomers thereof; or a pharmaceutically acceptable salt thereof.

The compounds of Formula I and Formula II are valuable inhibitors of gelatinase A and/or stromelysin-1. It has been shown previously that inhibitors of matrix metalloproteinses have efficacy in models of disease states like arthritis and metastasis that depend on modification of the extracellular matrix.

In vitro experiments were carried out which demonstrate the efficacy of compounds of Formula I and Formula II as potent and specific inhibitors of gelatinase A and stromelysin-1. Experiments were carried out with the catalytic domains of the proteinases. Table 1 shows the activity of Examples 1–5 versus GCD (recombinant gelatinase A catalytic domain) and SCD (stromelysin-1 catalytic domain). IC$_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*", *Biochemistry*, 1992;31:11231–11235).

TABLE 1

| Example | IC$_{50}$ ($\mu$M) | |
| --- | --- | --- |
|  | GCD | SCD |
| 1 | 0.039 | 0.12 |
| 2 | 0.058 | 0.11 |
| 3 | 0.73 | 0.93 |
| 4 | 0.30 | 0.82 |
| 5 | 0.15 | 0.28 |
| 6 | 0.074 | 0.187 |
| 7 | 0.14 | 0.089 |
| 8 | 0.424 | 0.95 |
| 9 | 0.324 | 0.865 |
| 10 | 0.076 | 0.12 |
| 11 | 0.172 | 1.81 |
| 12 | 0.0709 | 0.281 |
| 13 | 0.0855 | 0.123 |
| 14 | 0.0336 | 0.0499 |
| 15 | 0.221 | 0.953 |
| 16 | 0.12 | 0.167 |
| 17 | 0.057 | 0.14 |
| 18 | 0.96 | 2.39 |
| 19 | 0.052 | 0.097 |
| 20 | 0.0889 | 0.0839 |
| 21 | 0.0411 | 0.0668 |
| 22 | 0.05 | 0.088 |
| 23 | 6.8 | 3.9 |
| 24 | 1.9 | 2 |

Experimental Autoimmune Encephalomyelitis (EAE)

Compounds were administered by oral route to mice sensitized with a fragment of mouse myelin basic protein to induce EAE. Mice were dosed daily for 21 days beginning 4 hours before sensitization on day one. EAE responses of compound treated groups were compared to those of a control group of mice sensitized identically and a sham-sensitized group treated with vehicle. The values reported in Table 2 include responses during compound treatment only.

Methods

Sensitization Female mice [PL/J(F1)×SJL/J. Jackson Labs], 11 weeks old, were sensitized s.c. (0.05 cc×2) at the base of the tail with an emulsion containing equal parts of mouse myelin basic protein (MBP) fragment (amino acids 1–9 of the N-terminus of MBP) in saline and Difco Complete Freund's Adjuvant (CFA) fortified with heat killed desiccated Mycobacteria tuberculosis (MT). Each mouse received 300 μg of MBP fragment (230 μg free base) and 200 μg MT followed by retrobulbar (IV) injection of 200 ng of B. pertussis toxin in 0.2 cc of saline. Two days later mice receive a second injection of B. pertussis toxin.

Neurological Assessment Animals were weighted and evaluated for symptoms of EAE before and frequently after sensitization. EAE score: (0.5=slight limp tail, 1=limp tail or slow to right, 1.5=slight limp tail and slow to right, 2=paresis/mild paralysis or incontinence, 2.5=mild paralysis and slow to right or complete paralysis (one hind limb), 3=hind limb paralysis (both), 3.5=hind limb paralysis (both) and limp torso; 4=additional force limb paralysis, 4.5=head movement only, 5=moribund, death after previous EAE symptoms). Evaluators were blinded as to compound treatments and previous behavioral scores.

Disease symptoms are compared among groups for EAE severity, incidence, time to onset, cumulative score, and deaths, Peak EAE score: the mean of the highest score for each mouse in a group, independent of duration of symptoms; EAE incidence: the mean number of mice showing symptoms of EAE, defined as having EAE scores on any 3 consecutive days that total ">3.0". EAE deaths: an animal that died must have presented previous evidence of an EAE score greater than 0.5; EAE onset: the first of a 3-day series scoring a total of $\geq 3.0$.

A Cumulative EAE score is calculated for each animal. A mean of all animals' cumulative scores is then determined for each day.

Experimental groups were assumed to be similar and were compared for statistical significance by a 2-tailed T-Test ($p \leq 0.05$).

Compound was homogenized manually with an aliquot of warm vehicle (1.0% hydroxypropyl-methylcellulose [Sigma] in water) in glass mortar tubes and homogenizing pestle. The smooth compound paste was gradually suspended in vehicle. Mice were dosed with compound and/or vehicle, 10 mL/kg in groups of ten. A sham-sensitized group was similarly dosed with vehicle.

Results

Example 1, dosed at 50 mg/kg, delayed the onset of EAE for 4 days. Example 1 also reduced the EAE cumulative score (Table 2). There were no EAE-induced deaths (to Day 43) in the Example 1 treated group.

TABLE 2

Mouse Experimental Autoimmune Encephalomyelitis (EAE)

| Treatment/ Oral Dose | Peak EAE Score | EAE Incidence | EAE Onset (Day) | EAE Deaths | EAE Cumulative Score |
|---|---|---|---|---|---|
| Sham | 0.2 ± 0.1 p ≦ 0.05* | 0/10 | | 0/10 | 0.3 ± 0.2 p ≦ 0.05* |
| Control | 4.2 ± 0.1 | 10/10 | 12.2 ± 0.9 | 2/10 | 31.6 ± 1.7 |
| Example 1, 50 mg/kg | 3.8 ± 0.3 | 9/10 | 16.2 ± 1.0 p ≦ 0.05* | 0/10 | 17.9 ± 2.8 p ≦ 0.05* |

*Inhibition, 2-tailed T-test vs control

Streptococcal Cell Wall Model (SCW)

Female Lewis rats (125–150 g) are sensitized to the 100P preparation of streptococcal cell walls (obtained from Lee Labs, Greyson, Ga.) with an intra-articular injection to 10 μL SCW containing 6 μg of the cell wall particles into one of the ankle joints. The contralateral ankle joint is injected with an equal volume of saline. Twenty-one days later, animals are placed in treatment groups (7 per group) according to their intermediate response to the intra-articular injection of SCW (to obtain groups with equivalent responses). A control group is injected with saline. Each animal is then lightly anesthetized with ether, the paw volumes of each hind paw are determined by mercury plethysmography, and the animals are injected IV via the tail vein with a 0.25-mL dose of SCW containing 100 μg of the 100P cell wall particles. Each group of rats receives an oral dose of compound for 7 days in an appropriate dosing vehicle beginning on Day 21.

Paw swelling is determined by subtracting the paw volume of the saline injected ankle from the SCW sensitized ankle. Percent inhibition is calculated by comparing the compound treatment group with the control group. A one-way analysis of variance with a Dunnett's test for multiple comparisons is used for determination of statistical power.

TABLE 3

Inhibition of SCW-Induced Hindpaw Edema by Example 1

| Dose (mg/kg bid) | % Inhibition at Day 4 |
|---|---|
| 3 | 71 |
| 10 | 86 |
| 30 | 86 |

Rats were sensitized 21 days prior to initiating the flare response by systemic SCW. Example 1 was given 1 hour before to SCW and again 2 hours later for 4 consecutive days. Paw volume was measured 24 hours after the first administration. Numbers represent the mean percent inhibition of swelling from 10 animals/treatment group.

Adjuvant Arthritis Model

Polyarthritis was induced by a modified method of the procedure developed by Chang, et al., *Arthritis and Rheum.*, 1980;23:62. Briefly, male Wistar rats (100–115 g each) received subcutaneous injection of 0.1 mL of 10 mg/mL (or 1 mg) *Mycobacterium butyricum* suspended in paraffin oil in the distal third of the tail, using a glass tuberculin syringe and 25 gauge needle. *M. Butyricum* suspension was achieved by sonication in paraffin oil for 10 minutes with the vessel immersed in ice bath. Rates were randomized after injection and placed in cages. On Day 12 following immunization, rats with the highest paw swelling as well as those that showed no swelling at all were culled. The rest were randomized and separated into dosing (test) groups (N=10 per group) and control (vehicle) group (N=20). The hind paws volume and the weights of each animal in each group was recorded and served as the initial values for the study. Hind paws swelling was assessed using mercury plethysmography beginning on Day 12 on every other day till Dec.22 (final assessment).

Example 1 was tested at 6, 20, and 60 mg/kg divided into two equal doses per day and suspended in 1% methyl cellulose (2% viscosity, 1500 centipoises, Sigma). The dose volume was 10 mL/kg PO. Animals were dosed twice daily for 10 days starting on Day 12. Also, hind paw volumes were measured on Days 12, 14, 16, 18, 20, and 22 as stated above. The results are reported as % inhibition of delta edema on Day 22. Delta edema is the difference in footpad edema between the day in which animals are assessed and that on Day 12 of the study. The percent inhibition is based on a comparison of the treatment groups to the vehicle group.

TABLE 4

Inhibition of Adjuvant Arthritis by Example 1

| Dose (mg/kg bid) | % Inhibition | P-value |
|---|---|---|
| 3.0 | 68.1 | <0.001 |
| 10.0 | 84.4 | <0.001 |
| 30.0 | 99.9 | <0.001 |

Acetic Acid-Induced Hyperalgesia Model

Male Swiss-Webster mice (20–30 g) were pretreated orally with vehicle or Example 1 (0.03–10 mg/kg) 1 hour before the administration of 0.6% acetic acid (10 mL/kg i.p., in saline). Treatment groups (n=8) were divided so that 2 animals were placed into each of four 4"×4"×4" adjacent plexiglass containers. Seven minutes after acid, writing motions (abdominal contractions, concave arching of the back, and/or hindleg stretching) were tallied for 5 minutes. The $ID_{40}$ value was calculated by linear regression analysis.

TABLE 5

Inhibition of Acetic Acid-Induced Hyperalgesia by Example 1

| Dose (mg/kg) | % Inhibition | $ID_{40}$ (mg/kg) |
|---|---|---|
| 0.03 | 7 | |
| 0.1 | 26 | |
| 0.3 | 37 | 0.65 |
| 1 | 41 | |
| 10 | 65 | |

The following list contains abbreviations and acronyms used within the schemes and text:

| | |
|---|---|
| CDI | 1,1'-Carbonyl diimidazole |
| $CH_2Cl_2$ | Dichloromethane |
| CNS | Central nervous system |
| EAE | Experimental autoimmune encephalomyelitis |
| MMP | Matrix metalloproteinase |
| VSMC | Vascular smooth muscle cell |
| EtOH | Ethanol |
| HCl | Hydrogen chloride |
| $IC_{50}$ | Concentration of compound required to inhibit 50% of enzyme activity |
| KHMDS | Potassium hexamethyldisilazide |
| KOH | Potassium hydroxide |
| LiOH | Lithium hydroxide |
| MeOH | Methanol |
| n-BuLi | n-butyl lithium |
| THF | Tetrahydrofuran |
| TIMPs | Tissue inhibitors of metalloproteinases |
| $H_2NOH$ | Hydroxylamine |
| $H_2S$ | Hydrogen sulfide |
| $Bu_3SnCl$ | Tributyltin chloride |
| $AlCl_3$ | Aluminum chloride |
| $FeCl_3$ | Ferric chloride |
| $VCl_3$ | Vanadium chloride |
| $ZnCl_2$ | Zinc chloride |
| $MnCl_2$ | Manganese chloride |
| CuCN | Copper (I) cyanide |
| $Na_2CO_3$ | Sodium carbonate |
| KBr | Potassium bromide |
| $K_2CO_3$ | Potassium carbonate |
| $NaNO_2$ | Sodium nitrite |
| $NaHCO_3$ | Sodium bicarbonate |
| NBS | N-Bromosuccinimide |
| NFSI | N-Fluorodibenzenesulfonamide |

-continued

| | |
|---|---|
| TFA | Trifluoroacetic acid |
| TfOH | Trifluoromethanesulfonic acid |
| $Tf_2O$ | Trifluoromethanesulfonic anhydride |
| HBr | Hydrogen bromide |
| TEA | Triethylamine |
| Me | Methyl |
| Et | Ethyl |
| tBu | t-butyl |
| Bn | Benzyl |
| $PhNO_2$ | Nitrobenzene |
| $H_2O_2$ | Hydrogen peroxide |
| $(COCl)_2$ | Oxalyl chloride |
| $CCl_4$ | Carbon tetrachloride |
| $B(OMe)_3$ | Trimethylborate |
| $BF_3 \cdot OEt_2$ | Boron triflouride etherate |
| $Fe(acac)_3$ | Iron(III)acetylacetonate |
| $PdCl_2(PPh_3)_2$ | Bis(triphenylphosphine)palladium(II)chloride |
| $Pd(PPh_3)_4$ | Tetrakis(triphenylphosphine)palladium(0) |
| Ph | Phenyl |
| DAST | Diethylamino sulfur trifluoride |
| DMF | Dimethylformamide |
| TMS-Cl | Chlorotrimethylsilane |
| $CDCl_3$ | Deuterated chloroform |
| DMSO-$d_6$ | Deuterated dimethylsulfoxide |
| $MgSO_4$ | Magnesium sulfate |
| $Na_2SO_4$ | Sodium sulfate |

Compounds of Formula I and Formula II wherein $R^{3a}$ and $R^{4a}$ are hydrogen, Z is

$R^5$ is OH or SH, and R, $R^1$, $R^2$, $R^3$, and $R^4$ are as defined above can be made by one of three general routes, as set forth in Scheme 1.

Route A involves reaction of a compound of Formula (2) with a suitable metallating agent such as, for example, n-butyl lithium, magnesium metal, and the like to generate an organolithium or organomagnesium salt in situ, followed by reaction of the salt with a suitable metallating reagent such as, for example, tri-(n-butyl)tin chloride, trimethylborate, and the like to give a compound of Formula (3). A compound of Formula (3) can be coupled with bromobenzene or trifluoromethylsulfonyloxybenzene in the presence of a suitable catalyst such as, for example, tetrakis(triphenylphosphine)palladium(O), bis(triphenylphosphine)palladium(II)chloride, and the like with or without sodium bicarbonate to give a compound of Formula (4). Alternatively, a compound of Formula (4) can be prepared by coupling a compound of Formula (5) with phenylboric acid or tributylphenyltin in the presence of a suitable catalyst such as, for example, tetrakis(triphenylphosphine)palladium (O), bis(triphenylphosphine)palladium(II)chloride, and the like with or without sodium bicarbonate. Alternatively, a compound of Formula (4) can be prepared by coupling a compound of Formula (5a) with benzene in the presence of a suitable diazotization reagent such as, for example, iso-amyl nitrite at temperatures between 0° C. to about reflux. A compound of Formula (4) can be acylated using Friedel-Crafts conditions with a compound of Formula (6), prepared according to known methods such as, for example, as reported by Beckett, et al., Synlett., 1993:137, or the corresponding anhydride of Formula (6) in the presence of a Lewis acid such as, for example, $FeCl_3$, $AlCl_3$, $ZnCl_2$, and the like either neat or in an inert solvent such as, for example, dichloromethane, nitrobenzene, and the like at about −40° C. to about 120° C. to give a compound of Formula (7). A compound of Formula (7) can be deprotected using standard methodology known to one skilled in the art to give the corresponding carboxylic acid, which then can be condensed with a compound of Formula (8) to give a compound of Formula 1a. Alternatively, a compound of Formula (7) can be deprotected using standard methodology known to one skilled in the art, and the resulting carboxylic acid coupled with hydrogen sulfide after pretreatment with a suitable coupling agent such as, for example, 1,1'-carbonyldiimidazole (CDI), isobutyryl chloride, and the like, and then condensed with a compound of Formula (8) to give a compound of Formula Ib.

Route B involves reaction of a compound of Formula (3), prepared according to Route A, with 4-bromo-trifluoromethylsulfonyloxybenzene in the presence of a suitable catalyst such as, for example, tetrakis(triphenylphosphine)palladium(O), bis(triphenylphosphine)palladium(II)chloride, and the like with or without sodium bicarbonate to give a compound of Formula (9). Alternatively, a compound of Formula (4) prepared as described for Route A can be reacted with bromine to give a compound of Formula (9). A compound of Formula (9) can be reacted with a suitable metallating agent such as, for example, n-butyl lithium and the like to generate an organolithium in situ, which in turn can be reacted with a suitable metallating agent such as, for example, $MnCl_2$, CuCN, $ZnCl_2$, $VCl_3$, and the like to generate a modified organometallic agent in situ, followed by reaction with a compound of Formula (6) to give a compound of Formula (7). Alternatively, a compound of Formula (9) can be reacted with a suitable metallating agent such as, for example, n-butyl lithium, magnesium metal, and the like to generate an organolithium or organomagnesium salt in situ, followed by reaction of the salt with a suitable metallating reagent such as, for example, tri-(n-butyl)tin chloride, trimethylborate, and the like to give a compound of Formula (10). A compound of Formula (10) can be coupled with a compound of Formula (6) in the presence of a suitable catalyst such as, for example, tetrakis(triphenylphosphine)palladium(O), bis(triphenylphosphine)palladium(II)chloride and the like with or without sodium bicarbonate to give a compound of Formula (7). A compound of Formula (7) can be converted to compounds of Formulas Ia and Ib according to the methods outlined for Route A.

Route C involves reaction of a compound of Formula (11) with a suitable metallating agent such as, for example, n-butyl lithium, magnesium metal, and the like to generate an organolithium or organomagnesium salt in situ, followed by reaction of the salt with a suitable tin metallating reagent such as, for example, tri-(n-butyl)tin chloride and the like to give a compound of Formula (12). A compound of Formula (12) can be coupled with a compound of Formula (6) in the presence of a suitable catalyst such as, for example, tetrakis(triphenylphosphine)palladium(O), bis(triphenylphosphine)palladium(II)chloride, and the like with or without sodium bicarbonate to give a compound of Formula (13). A compound of Formula (13) can be deprotected using standard methodology known to one skilled in he art to give the corresponding free phenol, which can be reacted with trifluoromethanesulfonic anhydride to give the corresponding trifluoromethylsulfonyloxy derivative, which can be coupled with a compound of Formula (3) in the presence of a suitable catalyst such as, for example, tetrakis(triphenylphosphine)palladium(O), bis(triphenylphosphine)palladium(II)chloride, and the like with or without sodium bicarbonate to give a compound of Formula (7). A compound of Formula (7) can be converted to compounds of Formulas Ia and Ib according to the methods outlined for Route A.

Specific compounds of the present invention can be prepared by various routes, all of which are generally known in the art. Compounds of Formula I and Formula II wherein $R^3, R^{3a}, R^4$, and $R^{4a}$ are hydrogen, Z is

$R^5$ is OH or SH, and R, $R^1$, and $R^2$ are as defined in Formula I can be synthesized according to the sequence described in Scheme 2.

In Scheme 2, a biphenyl (4), which can be purchased from commercial sources or synthesized as described in Scheme 1 or hereinafter in Scheme 5 and wherein R and $R^1$ are as defined in Formula I, is reacted with a suitable acid chloride such as, for example, 3-carbomethoxypropionyl chloride and the like in the presence of a Lewis acid catalyst such as, for example, aluminum chloride and the like in a suitable solvent such as, for example, dichloromethane, nitrobenzene, and the like at temperatures between about −40° C. and about 120° C. to give the keto-ester (14). The keto-ester (14) can be hydrolyzed to the corresponding keto-acid (15) by stirring in aqueous hydrochloric acid of a concentration between about 2 M and about 6 M and at temperatures between about 25° C. and about reflux or by reacting with an alkali metal hydroxide such as, for example, lithium hydroxide, sodium hydroxide, potassium hydroxide, and the like in a suitable solvent such as, for example, methanol, ethanol, aqueous tetrahydrofuran, and the like at temperatures between about 0° C. and about reflux followed by acidification. Alternatively, the biphenyl (4) can be reacted with succinic anhydride in the presence of a Lewis acid catalyst such as, for example, aluminum chloride and the like, in a suitable solvent such as, for example, dichloromethane, nitrobenzene, and the like at temperatures between about −40° C. and about 120° C. to give the keto-acid (15) in one step. The keto-acid (15) can be reacted with a compound of Formula (8) with or without a suitable base such as, for example, lithium carbonate, sodium carbonate, potassium carbonate, and the like in a suitable solvent such as, for example, ethanol, methanol, isopropanol, and the like at temperatures between about 25° C. and about reflux to give the carboxylic acid (16). Alternatively, the keto-acid (15) can be reacted with a suitable coupling agent such as, for example, CDI, N,N'-dicyclohexylcarbodiimide (DCC), isobutyryl chloride (i-$C_4H_9$OCOCl), and the like followed by hydrogen sulfide to give the keto-thioacid (17). The keto-thioacid (17) can be reacted with a compound of Formula (8) with or without a suitable base such as, for example, lithium carbonate, sodium carbonate, potassium carbonate, and the like in a suitable solvent such as, for example, ethanol, methanol, isopropanol, and the like at temperatures between about 25° C. and about reflux to give the thioacid (18).

Compounds of Formula I and Formula II wherein $R^{3a}$ and $R^{4a}$ are hydrogen, and Z is

$R^5$ is OH or SH, and R, $R^1$, $R^2$, $R^3$, and $R^4$ are as defined in Formula I and Formula II can be synthesized according to the sequence outlined in Scheme 3.

In Scheme 3, (R)- or (S)-4-benzyl-2-oxazolidinone can be reacted with an acid chloride (19), prepared using standard methodology known to one skilled in the art, in the presence of a non-nucleophilic base such as, for example, sodium hydride and the like in an inert solvent such as, for example, tetrahydrofuran and the like at temperatures between about −40° C. and about reflux to give the N-acyl-oxazolidinone (20). The N-acyl-oxazolidinone (20) can be reacted with a suitable base such as, for example, potassium hexamethyldisilazide (KHDMS), lithium diisopropylamide (LDA), and the like followed by a bromoester (21), prepared in racemic form by bromination of the corresponding ester (22) with a suitable brominating reagent such as, for example, N-bromosuccinamide (NBS) and the like in a suitable solvent such as, for example, carbon tetrachloride and the like in the presence of ultraviolet light and a peroxide such as, for example, benzoyl peroxide and the like or in chiral form by reaction of an amino acid (23) with sodium nitrite and potassium bromide in aqueous hydrobromic acid followed by reacting the resulting bromoacid with a suitable coupling agent such as, for example, CDI, DCC, i-$C_4H_9OCOCl$, and the like and reacting the activated acid with a suitable alcohol such as, for example, methanol, ethanol, benzyl alcohol, and the like to give a compound of Formula (24). A compound of Formula (24), which may exist as a mixture of diastereoisomers, can be purified by a suitable technique such as, for example, chromatography on silica gel, and the like to give pure stereosiomers, which can be reacted with lithium hydroperoxide in THF-water followed by reaction of the resulting carboxylic acid with oxalyl chloride to give the corresponding acid chloride (25).

The (4-(1,1-dimethylethyl)oxyphenyl)tributyltin (27) is synthesized as set forth in Scheme 3. The commercially available 4-bromophenol is reacted with isobutylene in the presence of an acid catalyst such as, for example, trifluoroacetic acid (TFA)/triethylamine (TEA), boron trifluoride-etherate ($BF_3.OEt_2$), and the like in a suitable solvent such as, for example, dichloromethane and the like to give the t-butyl ether (26). The t-butyl ether (26) is reacted with a suitable organolithium such as, for example, n-butyl lithium and the like in tetrahydrofuran (THF) at low temperature followed by tri-n-butyltin chloride to give the (4-(1,1-dimethylethyl)oxyphenyl)tributyltin (27). The (4-(1,1-dimethylethyl)oxyphenyl)tributyltin (27) is reacted with the acid chloride (25) in the presence of a suitable catalyst such as, for example, tetrakis(triphenylphosphine)palladium(O), bis(triphenylphosphine)palladium(II)chloride, and the like with or without sodium bicarbonate in a solvent such as, for example, THF, dioxane, and the like at temperatures between about −20° C. and about reflux to give the keto-ester (28). The keto-ester (28) is deprotected by reacting with TFA in the presence of a suitable carbonium ion scavenger such as, for example, anisole, thioanisole, triethylsilane, and the like in a solvent such as, for example, dichloromethane, chloroform, and the like, and the resulting phenol is reacted with trifluoromethanesulfonic anhydride to give the triflate (29). The triflate (29) is reacted with the phenylboric acid (30), prepared by reacting the bromobenzene (31) first with n-butyl lithium or t-butyl lithium in tetrahydrofuran at low temperatures followed by trimethylborate and acid hydrolysis, in the presence of a suitable catalyst such as, for example, tetrakis(triphenylphosphine) palladium(O), bis(triphenylphosphine)palladium(II) chloride, and the like with or without sodium bicarbonate in a solvent such as, for example, THF, dioxane, and the like at temperatures between about −20° C. and about reflux to give the keto-ester (32). Alternatively, the triflate (29) can be reacted with the phenyltributyltin (33), prepared by reacting the bromobenzene (31) first with n-butyl lithium or t-butyl lithium in tetrahydrofuran at low temperatures followed by tri-n-butyltin chloride, in the presence of a suitable catalyst such as, for example, tetrakis(triphenylphosphine)palladium (O), bis(triphenylphosphine)palladium(II)chloride with or without sodium bicarbonate in a solvent such as, for example, THF, dioxane, and the like at temperatures between about −20° C. and about reflux to give the keto-ester (32). The keto-ester (32) can be hydrolyzed to the corresponding keto-acid by stirring in aqueous hydrochloric acid at a concentration between about 2 M and about 6 M and at temperatures between about 25° C. and about reflux or by reacting with an alkali metal hydroxide such as, for example, lithium hydroxide, sodium hydroxide, potassium hydroxide, and the like in a suitable solvent such as, for example, methanol, ethanol, aqueous tetrahydrofuran, and the like at temperatures between about 0° C. and about reflux, and the keto-acid can be reacted with a compound of Formula (8) with or without a suitable base such as, for example, lithium carbonate, sodium carbonate, potassium carbonate, and the like in a suitable solvent such as, for example, ethanol, methanol, isopropanol, and the like at temperatures between about 25° C. and about reflux to give the carboxylic acid (34). Alternatively, the keto-ester (32) can be hydrolyzed to the corresponding keto-acid by stirring in aqueous hydrochloric acid at a concentration between about 2 M and about 6 M and at temperatures between about 25° C. and about reflux or by reacting with an alkali meal hydroxide such as, for example, lithium hydroxide, sodium hydroxide, potassium hydroxide, and the like in a suitable solvent such as, for example, methanol, ethanol, aqueous tetrahydrofuran, and the like at temperatures between about 0° C. and about reflux, and the keto-acid can be reacted with a suitable coupling agent such as, for example, CDI, DCC, i-$C_4H_9OCOCl$, and the like followed by hydrogen sulfide to give the keto-thioacid, which in turn can be reacted with a compound of Formula (8) with or without a suitable base such as, for example, lithium carbonate, sodium carbonate, potassium carbonate and the like in a suitable solvent such as, for example, ethanol, methanol, isopropanol and the like at temperatures between about 25° C. and about reflux to give the thioacid (35).

Alternatively, compounds of Formula I and Formula II wherein $R^{3a}$ and $R^{4a}$ are hydrogen, and Z is

$R^5$ is OH or SH, and R, $R^1$, $R^3$, and $R^4$ are as defined in Formula I and Formula II can be synthesized according to the sequence outlined in Scheme 4.

In Scheme 4, the phenylboric acid (36) or the phenyltributyltin (33), prepared as described in Scheme 3, is reacted with 4-bromo-trifluoromethyl-sulfonyloxybenzene (37), prepared by reacting 4-bromophenol with trifluoromethanesulfonic anhydride in dichloromethane, in the presence of a suitable catalyst such as, for example, tetrakis (triphenylphosphine)palladium (0), bis(triphenylphosphine) palladium(II)chloride, and the like with or without sodium bicarbonate in a solvent such as, for example, THF, dioxane, and the like at temperatures between about −20° C. and about reflux to give the biphenyl (9). The biphenyl (9) can be reacted with a suitable metallating agent such as, for example, n-butyl lithium and the like in a suitable solvent such as, for example, THF and the like at low temperatures to generate an organolithium in situ, which in turn can be reacted with a suitable metallating agent such as, for example, MnCl$_2$, CuCN, ZnCl$_2$, VCl$_3$, and the like to generate a modified organometallic agent in situ, which in turn can be reacted with an acid chloride (25) in the presence of lithium bromide with or without an additional Lewis acid such as, for example, iron(III)acetylacetonate (Fe(acac)$_3$) to give the keto-ester (32). Alternatively, the biphenyl (9) can be reacted with a suitable metallating agent such as, for example, n-butyl lithium and the like in a suitable solvent such as, for example, THF and the like at low temperatures to generate an organolithium in situ, which in turn can be reacted with a Weinreb amide (38), prepared by reacting the acid chloride (25) with N,O-dimethylhydroxylamine hydrochloride in the presence of a base such as, for example, triethylamine, diisopropylethylamine, and the like in a suitable solvent such as, for example, dichloromethane, THF, and the like at temperatures between about −78° C. and about 25° C., to give the keto-ester (32). In a second alternative approach, the biphenyl (9) can be reacted with a suitable metallating agent such as, for example, n-butyl lithium and the like in a suitable solvent such as, for example, THF and the like at low temperatures to generate an organolithium in situ, which in turn can be reacted with tri-n-butyltin chloride to give the biphenyltin (10). The biphenyltin (10) can be reacted with the acid chloride (25) in the presence of a suitable catalyst such as, for example, tetrakis(triphenylphosphine)palladium(0), bis(triphenylphosphine)-palladium(II)chloride, and the like with or without sodium bicarbonate in a solvent such as, for example, THF, dioxane, and the like at temperatures between about −20° C. and about reflux to give the keto-ester (32). The keto-ester (32) so made can be converted to the carboxylic acid (34) or thioacid (35) according to the procedures described in Scheme 3.

Alternatively, compounds of Formula I and Formula II wherein R$^{3a}$ and R$^{4a}$ are hydrogen, and Z is

R$^5$ is OH or SH, and R, R$^1$, R$^3$, and R$^4$ are as defined in Formula I and Formula II can be synthesized according to the sequence outlined in Scheme 5.

In Scheme 5, the phenol (39) is reacted with trifluoromethanesulfonic anhydride in a suitable solvent such as, for example, dichloromethane at temperatures between about −40° C. and about reflux to give the triflate (40). The triflate (40) is reacted with phenylboric acid or tri-n-butylphenyltin in the presence of a suitable catalyst such as, for example, tetrakis(triphenylphosphine)palladium(0), bis(triphenylphosphine)palladium(II)chloride, and the like with or without sodium bicarbonate in a solvent such as, for example, THF, dioxane, and the like at temperatures between about −20° C. and about reflux to give the biphenyl (4). Alternatively, the phenylboric acid (30) or phenylbributyltin (33) is reacted with bromobenzene or trifluoromethylsulfonyloxybenzene in the presence of a suitable catalyst such as, for example, tetrakis(triphenylphosphine)palladium (0), bis(triphenylphosphine)palladium(II)chloride, and the like with or without sodium bicarbonate in a solvent such as, for example, THF, dioxane and the like at temperatures between about −20° C. and about reflux to give the biphenyl (4). The biphenyl (4) is reacted with an acid chloride (25) in the presence of a Lewis acid catalyst such as, for example, aluminum chloride and the like in a suitable solvent such as, for example, dichloromethane, nitrobenzene, and the like at temperatures between about −40° C. and about 120° C. to give the keto-ester (32). The keto-ester (32) so made can be converted to the carboxylic acid (34) or thioacid (35) according to the procedures described in Scheme 3.

Alternatively, compounds of Formula I and Formula II wherein Z is

R$^5$ is OH or SH, and R, R$^1$, R$^2$, R$^3$, R$^{3a}$, R$^4$, and R$^{4a}$ are as defined in Formula I and Formula II can be synthesized according to the sequence outlined in Scheme 6.

In Scheme 6 the biphenyl (4), prepared according to the procedures outlined in Schemes 1 or 5, is allowed to react with a suitable acrylating agent such as, for example, the acid chloride of Formula (19) and the like in the presence of a Lewis acid such as, for example, FeCl$_3$, AlCl$_3$, ZnCl$_2$, and the like either neat or in an inert solvent such as, for example, dichloromethane, nitrobenzene, and the like at about −40° C. to about 120° C. to give a compound of Formula (41). A compound of Formula (41) is allowed to react with a suitable strong base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (42), or N-fluorodibenzenesulfonamide (NFSI) for R$^{3a}$ equals fluorine, at temperatures at about −78° C. to about 50° C. to give a compound of Formula (43). A compound of Formula (43) is allowed to react with a suitable strong base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (44) to give a compound of Formula (45). A compound of Formula (45) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of Formula (46). A compound of Formula (46) is condensed with a compound of Formula (8) to give a compound of Formula (Ic). Alternatively, a compound of Formula (46) is allowed to react with hydrogen sulfide after pretreatment with a suitable coupling agent such as, for example, 1,1'-carbonyldiimidazole (CDI), N,N'-dicyclohexylcarbodiimide, isobutyryl chloride, and the like, and then condensed with a compound of Formula (8) to give a compound of Formula (Id).

Alternatively, a compound of Formula (45) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (47) or NFSI for R$^4$ equals fluorine, at temperatures at about −78° C. to about 50° C. to give a compound of Formula (48). A compound of Formula (48) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of Formula (49). A compound of Formula (49) is converted to compounds of Formulas (Ie) and (If) according to the procedure described for the conversion of a compound of Formula (46) to compounds of Formulas (Ic) and (Id), respectively. Alternatively, a compound of Formula (48) is allowed to react with a suitable base such as, for example, n-butyl lithium, lithium diispropylamide, potassium hexamethyldisilazide, and the like in an inert solvent such as, for example, tetrahydrofuran, diethyl ether, and the like at about −78° C. to about 25° C. followed by a suitable alkylating agent of Formula (50) or NFSI for $R^{4a}$ equals fluorine, at temperatures at about −78° C. to about 50° C. to give a compound of Formula (51). A compound of Formula (51) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of Formula (52). A compound of Formula (52) is converted to compounds of Formulas (Ig) and (Ih) according to the procedure described for the conversion of a compound of Formula (46) to compounds of Formulas (Ic) and (Id), respectively.

Alternatively, compounds of Formula I and Formula II wherein Z is

$R^5$ is OH or SH, and R, $R^1$, $R^2$, $R^3$, $R^{3a}$, $R^4$, and $R^{4a}$ are as defined in Formula I and Formula II are synthesized according to the sequence outlined in Scheme 7.

In Scheme 7, a compound of Formula (53) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (50) or NFSI for $R^{4a}$ equals fluorine, at temperatures at about −78° C. to about 50° C. to give a compound of Formula (54). A compound of Formula (54) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (55), prepared by allowing a compound of Formula (4), prepared according to the method outlined in Scheme 5, with a suitable acylating agent such as $BrCH_2COICl$ in the presence of a suitable Lewis acid such as, for example, $FeCl_3$, $AlCl_3$, $ZnCl_2$, and the like either neat or in an inert solvent such as, for example, dichloromethane, nitrobenzene, and the like at about −40° C. to about 120° C., to give a compound of Formula (56). A compound of Formula (56) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid can be resolved using methods known to one skilled in the art to give a compound of Formula (57). A compound of Formula (57) is converted to compounds of Formulas (Ii) and (Ij) according to the procedure described in Scheme 6 for the conversion of a compound of Formula (46) to compounds of Formulas (Ic) and (Id), respectively. Alternatively, a compound of Formula (56) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (58), or NFSI for $R^3$ equals fluorine, at temperatures at about −78° C. to about 50° C. to give a compound of Formula (59). A compound of Formula (59) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid can be resolved using methods known to one skilled in the art to give a compound of Formula (60). A compound of Formula (60) is converted to compounds of Formulas (Ik) and (Il) according to the procedure described in Scheme 6 for the conversion of a compound of Formula (46) to compounds of Formulas (Ic) and (Id), respectively. Alternatively, a compound of Formula (59) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (42), or NFSI for $R^{3a}$ equals fluorine, at temperatures at about −78° C. to about 50° C. to give a compound of Formula (51). A compound of Formula (51) is converted via a compound of Formula (52) to compounds of Formulas (Ig) and (Ih) according to the procedure described in Scheme 6.

Compounds of Formula II wherein Z is CH(OH), C=S, $CF_2$, or CHF and $R^5$ is OH or SH, and R, $R^1$, $R^3$, $R^{3a}$, $R^4$, and $R^{4a}$ are as defined in Formula II are synthesized according to the sequence outlined in Scheme 8.

In Scheme 8, keto-esters of Formulas (7), (14), (32), (45), (48), (51), (56), or (59) can be hydrolyzed to the corresponding keto-acids, such as by stirring in aqueous hydrochloric acid at a concentration between about 2 M and about 6 M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification, and the keto-acids can be reduced using an appropriate hydride donating reagent such as sodium borohydride in ethanol, L- or S-selectride and the like in a suitable solvent such as, for example, toluene, tetrahydrofuran and the like to give the alcohol-acid (61). The alcohol-acid (61) can be silylated such as, for example, by allowing it to react with chlorotrimethylsilane (TMS-Cl) in the presence of a catalyst such as, for example, imidazole and the like in a suitable solvent such as, for example, anhydrous dimethylformamide (DMF) and the like to give the corresponding O-silyl alcohol-silyl ester, which can be fluorinated by allowing it to react with a suitable reagent such as, for example, diethylaminosulfur trifluoride (DAST) and the like in a suitable solvent such as, for example, dichloromethane, chloroform and the like at temperatures between about −20° C. and about reflux to give the corresponding fluoro-silyl ester, which can be hydrolyzed by stirring in aqueous hydrochloric acid at a concentration between about 2 M and about 6 M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification or by stirring in the presence of a suitable fluoride reagent such as, for example, tetra-n-butylammonium fluoride, aqueous hydrogen fluoride and the like in a suitable solvent such as, for example, tetrahydrofuran, acetonitrile and the like to give the fluoro-acid (62). The fluoro-acid (62) can be reacted with a suitable coupling agent such as, for example, CDI, DCC, i-C$_4$H$_9$OCOCl, and the like followed by hydrogen sulfide to give the fluoro-thioacid (63).

Alternatively, the keto-esters of Formulas (7), (14), (32), (45), (48), (51), (56), or (59) can be allowed to react with a suitable fluorinating agent such as, for example, DAST and the like in a suitable solvent such as, for example, dichloromethane, chloroform and the like at temperatures between about −20° C. and about reflux to give the corresponding fluoro-ester, which can be hydrolyzed such as by stirring in aqueous hydrochloric acid at a concentration between about 2 M and about 6 M and at temperatures between about 25° C. and reflux stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification to give the corresponding difluoro-acid (64). The difluoro-acid (64) can be allowed to react with a suitable coupling agent such as, for example, CDI, DCC, i-C$_4$H$_9$OCOCl, and the like followed by hydrogen sulfide to give the fluoro-thioacid (65).

Alternatively, keto-esters of Formulas (7), (14), (32), (45), (48), (51), (56), or (59) can be hydrolyzed to the corresponding keto-acids, such as by stirring in aqueous hydrochloric acid at a concentration between about 2 M and about 6 M and at temperatures between about 25° C. and reflux or by stirring in the presence of a suitable alkali metal hydroxide such as, for example, lithium, sodium or potassium hydroxide and the like in a suitable solvent such as, for example, methanol, ethanol or aqueous THF and the like at temperatures between about 0° C. and reflux followed by acidification, and the keto-acids allowed to react with a suitable sulfur reagent such as, for example, Lawesson's reagent and the like in a suitable solvent such as, for example, tetrahydrofuran and the like at temperatures between about 0° C. and reflux to give the thioketo-acid (66). The thioketo-acid (66) can be allowed to react with a suitable coupling agent such as, for example, CDI, DCC, i-C$_4$H$_9$OCOCl, and the like followed by hydrogen sulfide to give the thioketo-thioacid (67).

Compounds of Formula I and Formula II wherein R$^{3a}$ and R$^{4a}$ are hydrogen, Z is

R$^5$ is OH or SH, and R, R$^1$, R$^2$, R$^3$, and R$^4$ are as defined in Formula I can be synthesized according to the sequence outlined in Scheme 9.

In Scheme 9, bromobenzene can be acrylated using Friedel-Crafts conditions with a compound of Formula (6), which may be purchased from commercial suppliers or prepared according to known methods such as, for example, as reported by Beckett, et al., Synlett, 1993:137, in the presence of a Lewis acid such as, for example, FeCl$_3$, AlCl$_3$, ZnCl$_2$, and the like either neat or in an inert solvent such as, for example, dichloromethane, nitrobenzene, and the like at about −40° C. to about 120° C. to give a compound of Formula (68). A compound of Formula (68) can be condensed with a compound of Formula (30), prepared as described in Scheme 3, in the presence of a suitable catalyst such as, for example, tetrakis(triphenylphosphine)palladium (0), bis(triphenylphosphine)palladium(II)chloride, and the like optionally in the presence of aqueous sodium bicarbonate or aqueous sodium carbonate in a solvent such as, for example, toluene, tetrahydrofuran, dioxane, and the like at temperatures between about −20° C. and about reflux, or in the presence of palladium(II)acetate, tri(O-toluyl)phosphine and excess of a suitable amine base such as, for example, triethylamine, diisopropylethylamine, and the like, to give the keto-ester (7). The keto-ester (7) can be converted to a compound of Formula Ia or a compound of Formula Ib according to the procedures outlined in Scheme 1, Route A.

Compounds of Formula I wherein R$^5$ is R$^{5a}$, R$^2$ is OH, and R, R$^1$, R$^3$, R$^{3a}$, R$^4$, and R$^{4a}$ are as defined in Formula I can be synthesized according to the sequence outlined in Scheme 10.

In Scheme 10, oxime-acids of Formulas (Ia), (16), (34), (Ic), (Ie), (Ig), (Ii), and (Ik), wherein R$^2$ is OH, can be cyclized by stirring in a suitable solvent such as, for example, toluene, benzene, and the like at about reflux over a Dean-Stark trap to remove water, or by stirring in a suitable solvent such as, for example, tetrahydrofuran, dioxane, toluene, dichloromethane and the like which contains a dehydrating agent such as, for example, anhydrous magnesium sulfate, activated 3 angstrom molecular sieves, and the like at temperatures from about 0° C. to about reflux, in the presence of a suitable acid catalyst such as, for example, p-toluenesulfonic acid or methanesulfonic acid and the like to give a compound of the formula (69). Alternatively, the oxime-acids of Formulas (Ia), (16), (34), (Ic), (Ie), (Ig), (Ii), and (Ik) wherein R$^2$ is OH can be cyclized by reaction with a suitable carboxylic acid activating agent such as, for example, N,N'-dicyclohexylcarbodiimide, 1,1'-carbonyldiimidazole, isobutylchloroformate, 2-chloro-1-methyl-pyridinium iodide/triethylamine and the like in a suitable solvent such as, for example, tetrahydrofuran, dioxane, dichloromethane, and the like at about −20° C. to about reflux to give a compound of Formula (69). A compound of Formula (69) can be reacted with an alcohol of Formula R$^{5a}$OH (70), wherein R$^{5a}$ is as defined in Formula I, in a suitable solvent such as, for example, chloroform, tetrahydrofuran, dioxane, toluene and the like optionally in the presence of a suitable acid catalyst such as hydrogen chloride, p-toluenesulfonic acid, sulfuric acid and the like at temperatures from about 25° C. to about reflux to give compounds of Formulas (71) and (72), wherein the conformations of the oximes are designated as E and Z, respectively.

Alternatively, oxime-acids of Formulas (Ia), (16), (34), (Ic), (Ie), (Ig), (Ii), and (Ik), wherein R$^2$ is as defined in Formula I, and compounds of Formula II wherein Z is as defined in Formula II, can be allowed to react with 1 mol equivalent of a suitable base such as, for example, potassium or sodium hydroxide and the like in a suitable solvent such as, for example, acetone, ethanol, water, and the like followed by reaction with an alkyl carboxylic acid, halomethyl ester of Formula (73) such as, for example, 2,2-dimethyl-propionic acid, bromomethyl ester of 2,2-dimethyl-propionic acid, chloromethyl ester, and the like optionally in the presence of a suitable activating agent such as, for example, 10% aqueous sodium iodide, aqueous silver nitrate and the like, in a suitable solvent such as, for example, acetone at temperatures between about 0° C. and about reflux to give compounds of Formulas (74) and (75), wherein the conformations of the oximes are designated as E and Z, respectively, and (76).

Compounds of the formula $H_2NR^2$ can be obtained from commercial sources or prepared by methods generally known to one skilled in the art.

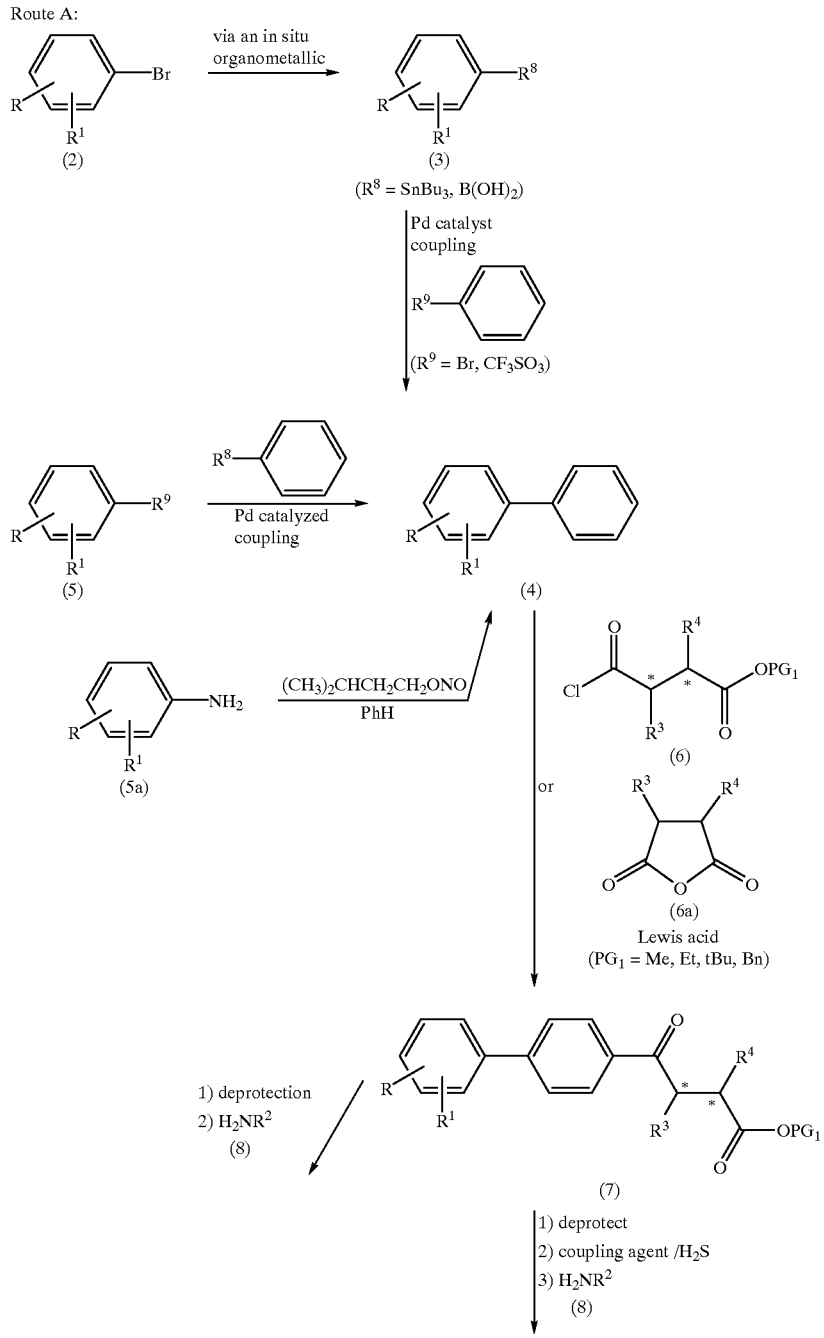

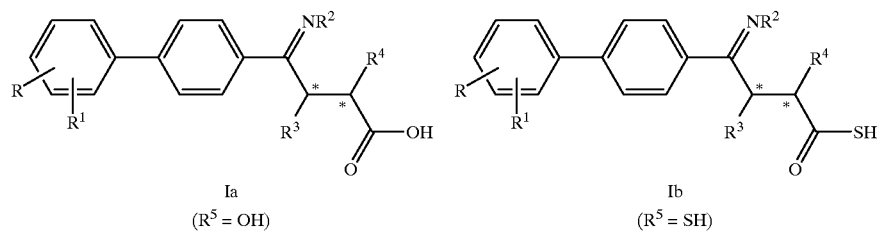
Ia (R⁵ = OH)   Ib (R⁵ = SH)
Route B:
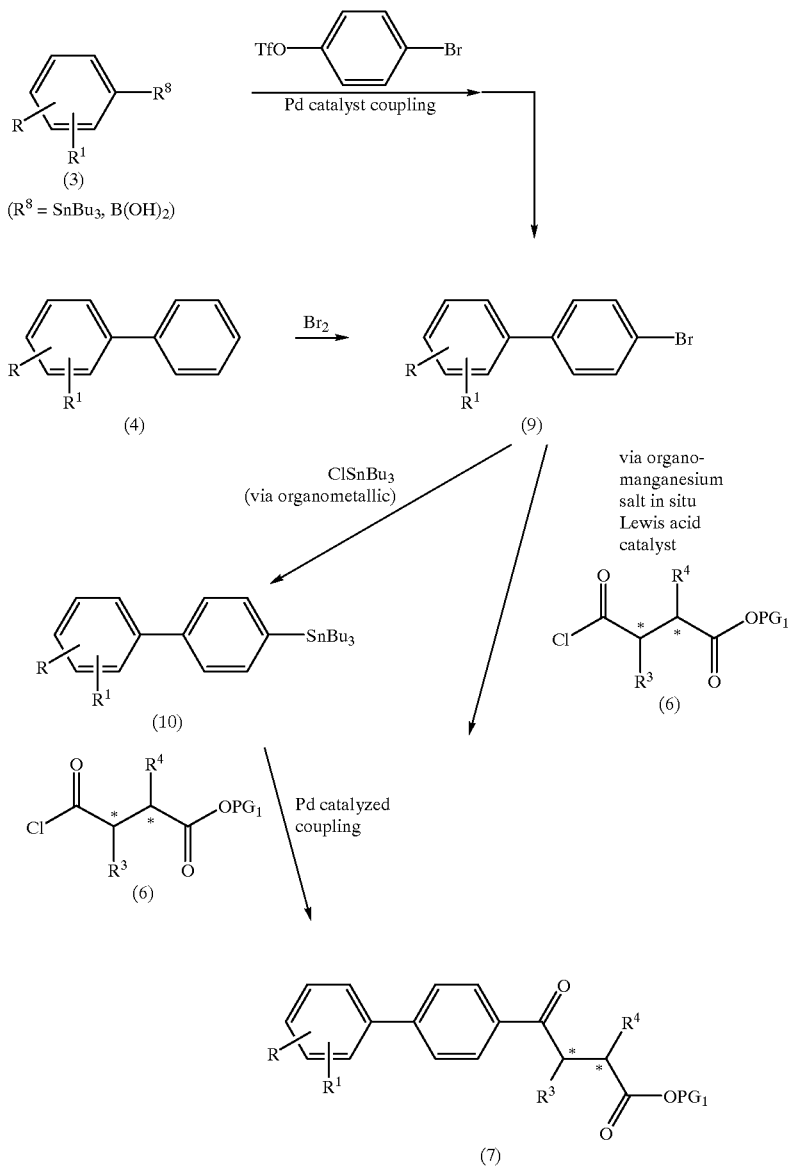

Route C:
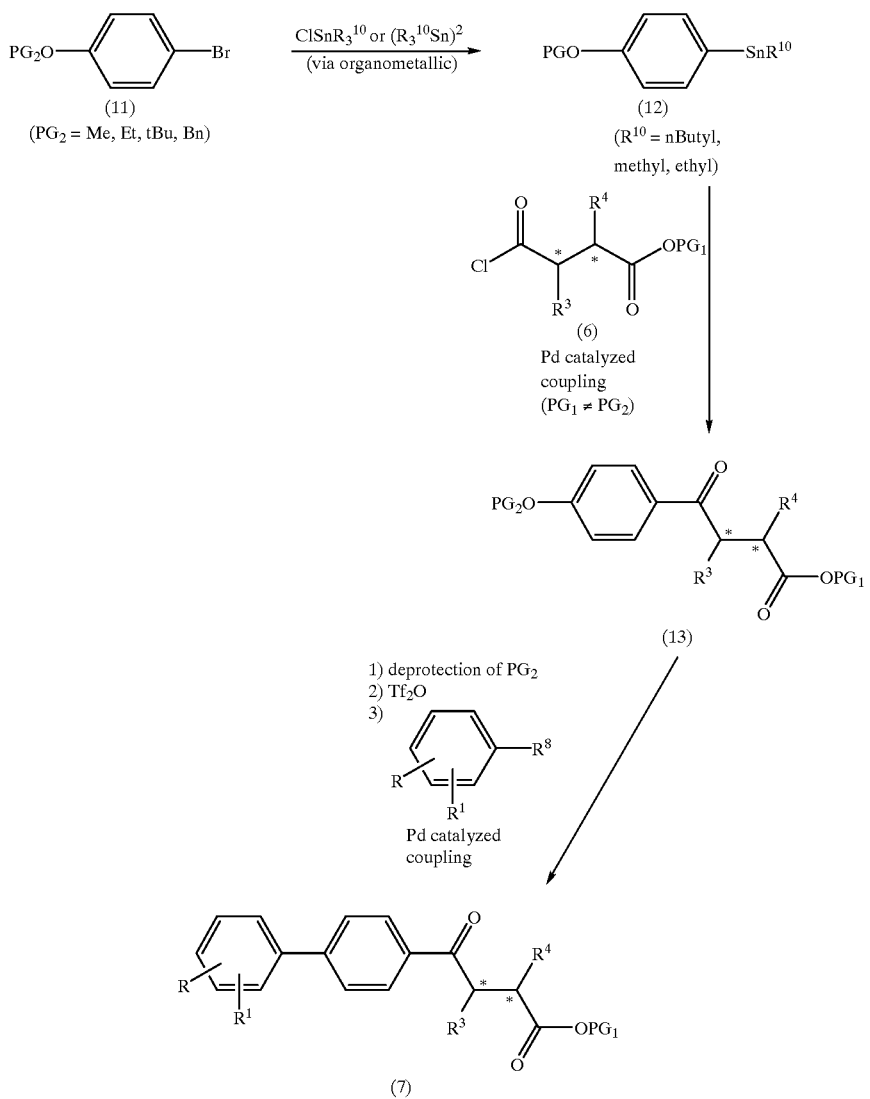
SCHEME 2
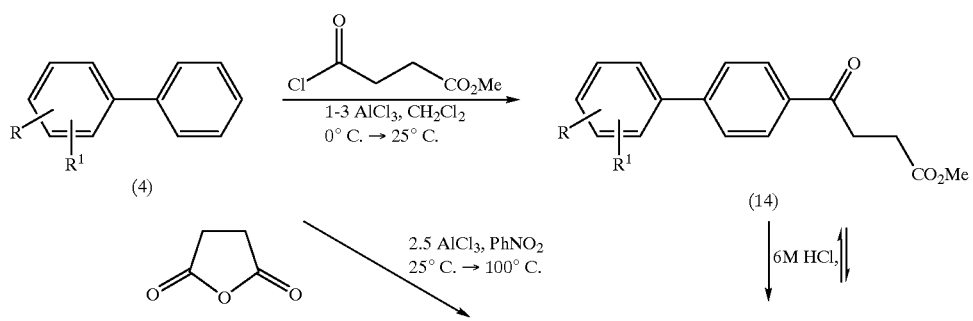

-continued
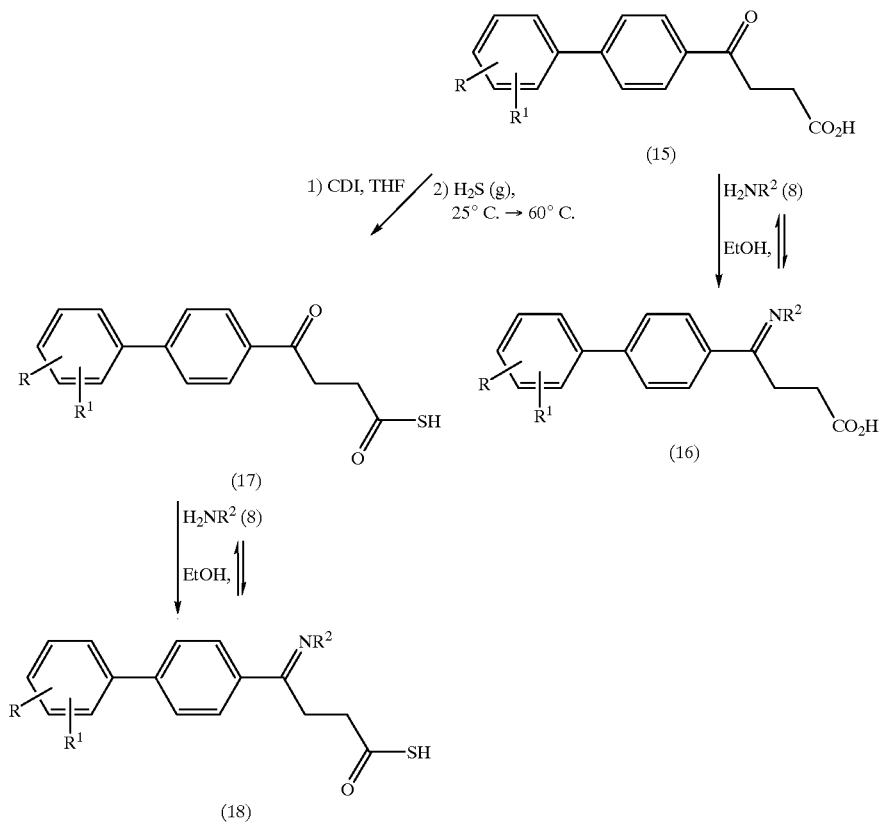
SCHEME 3
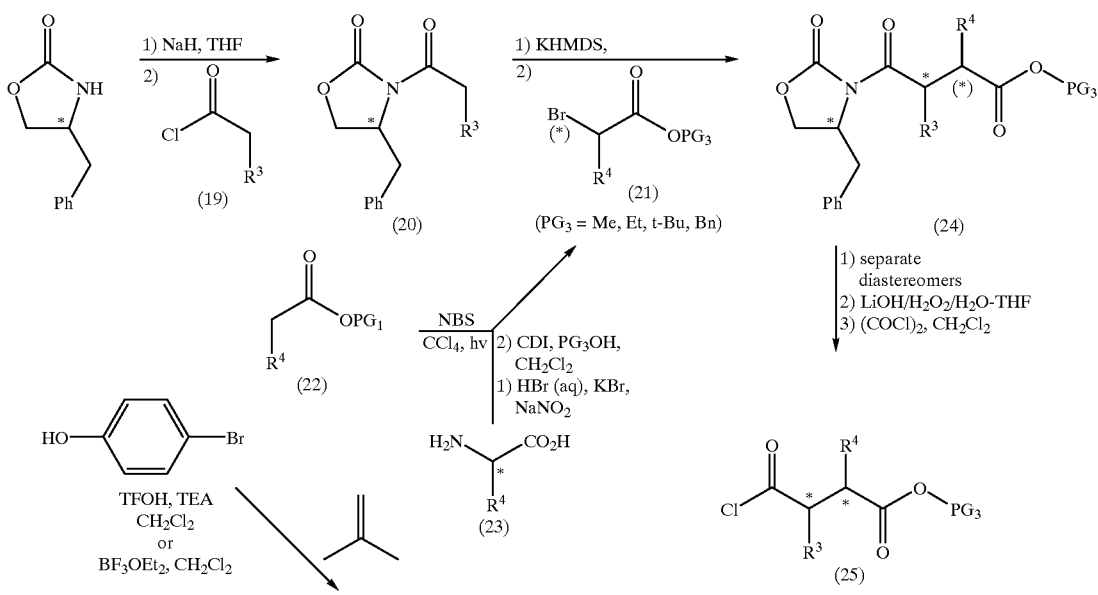

-continued
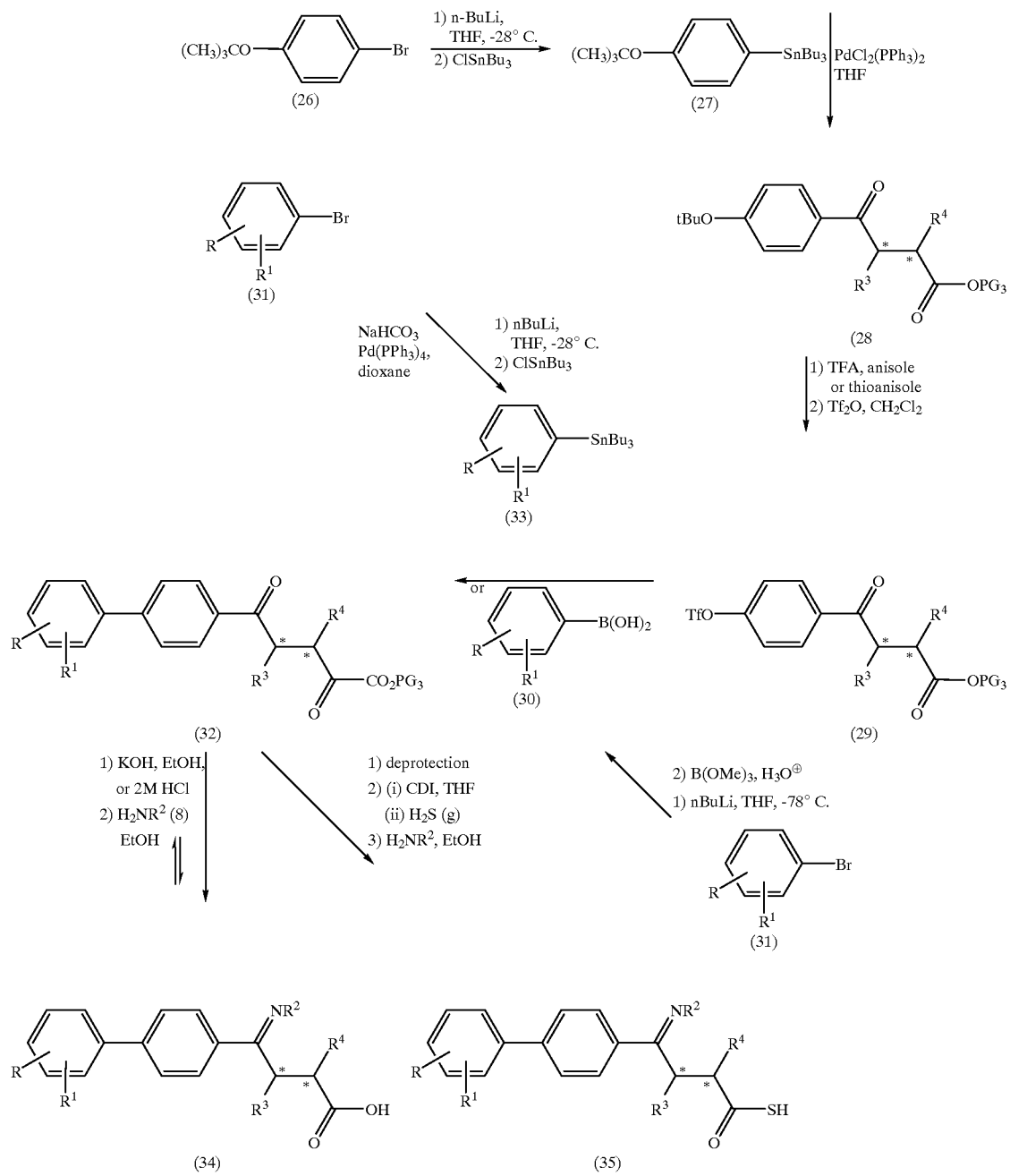

SCHEME 4
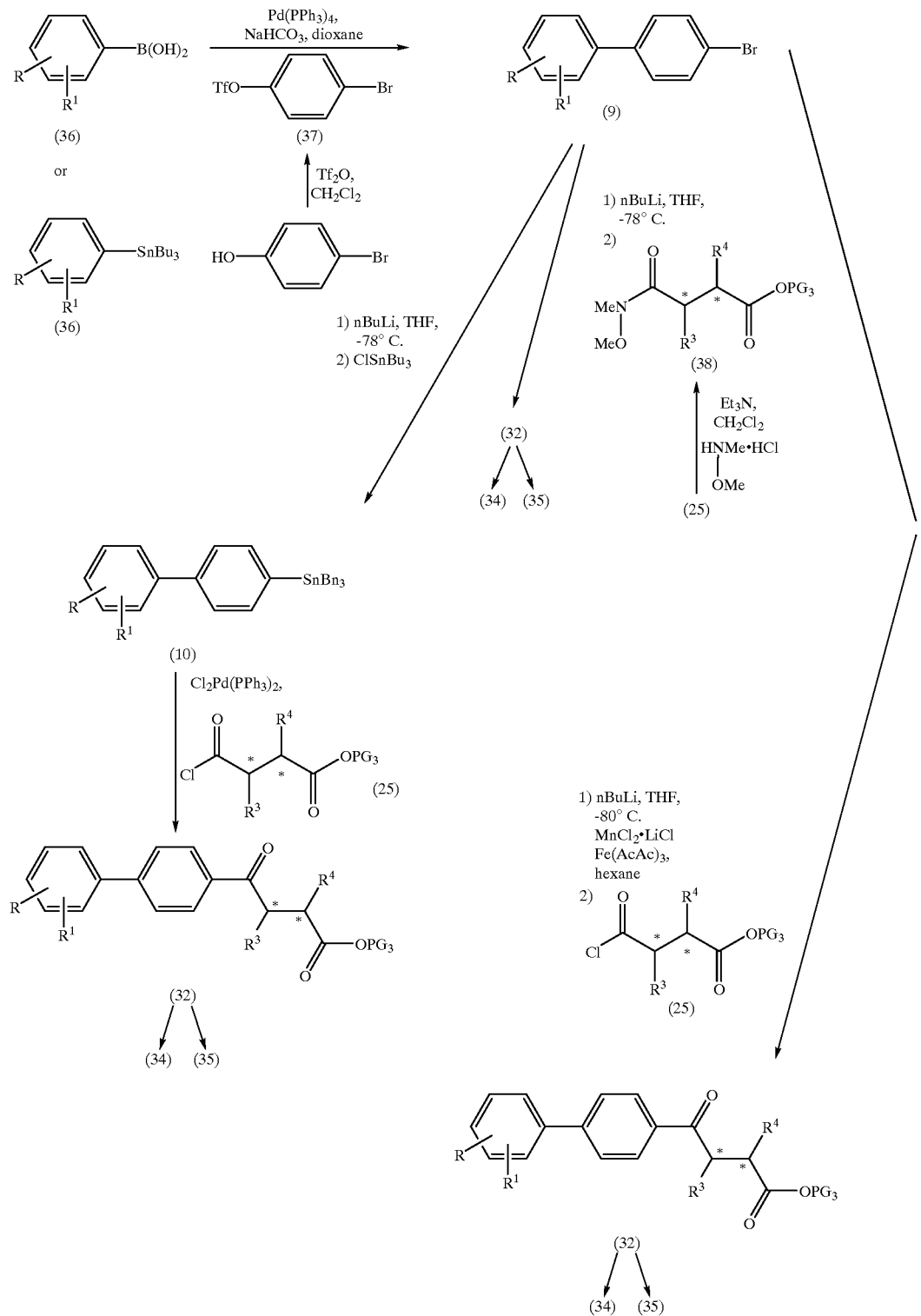

SCHEME 5
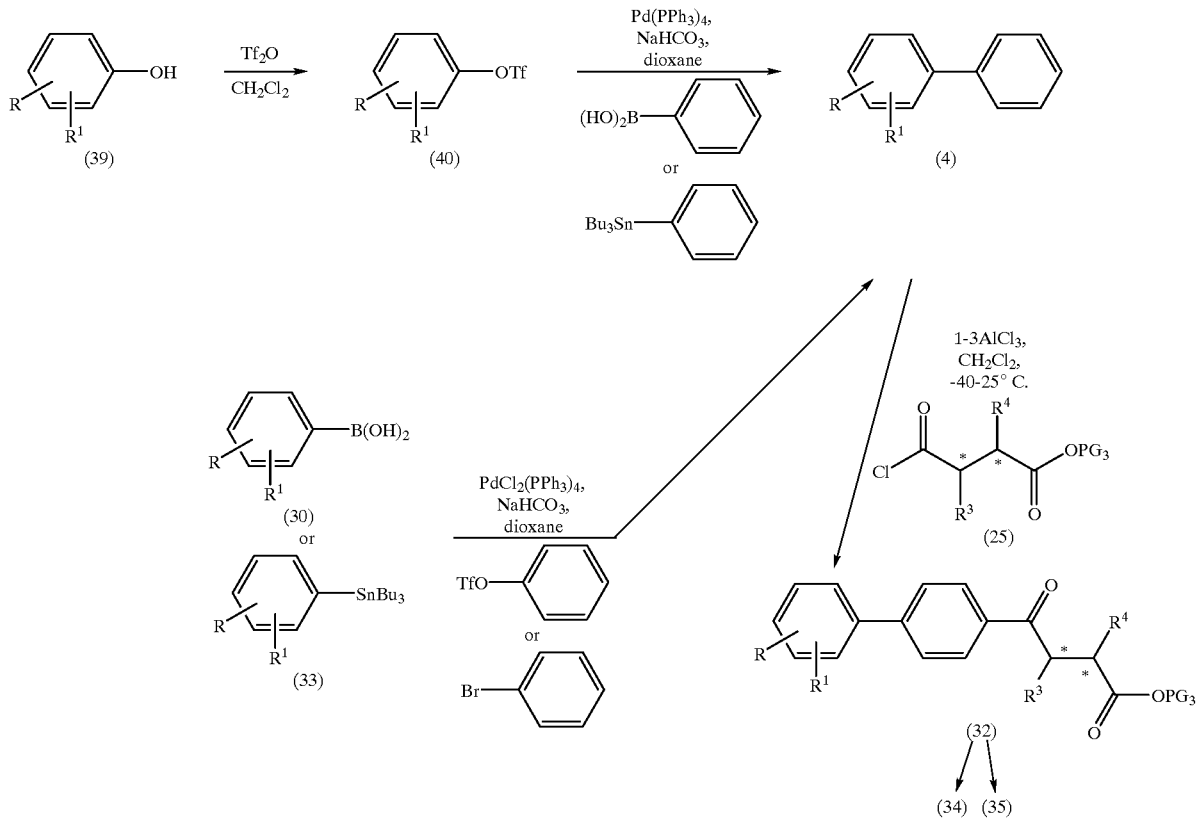
SCHEME 6
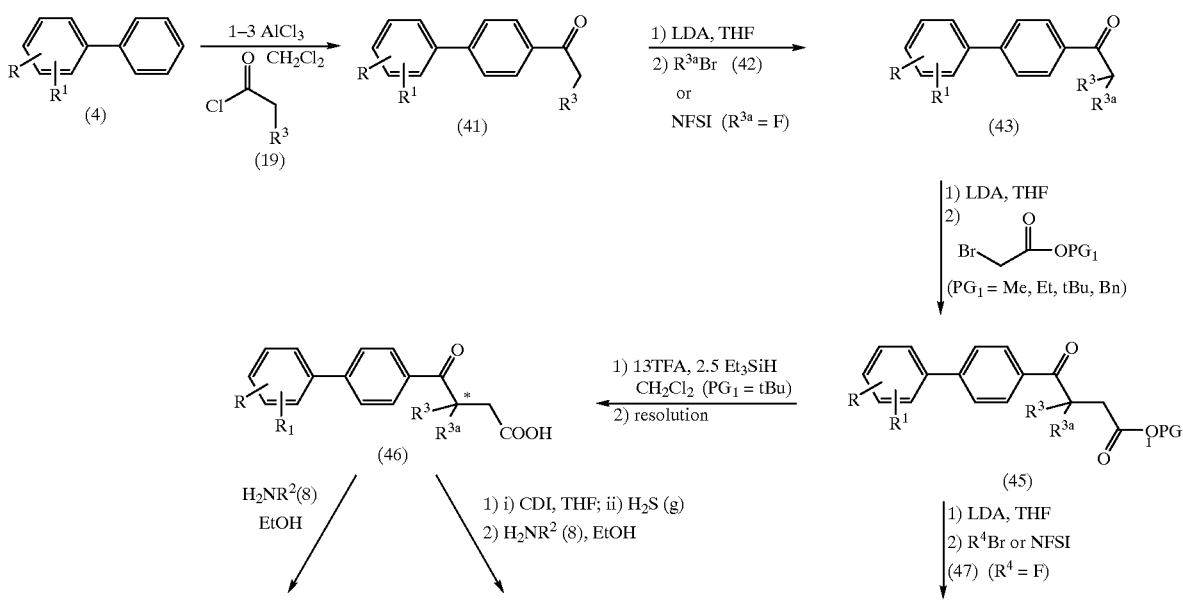

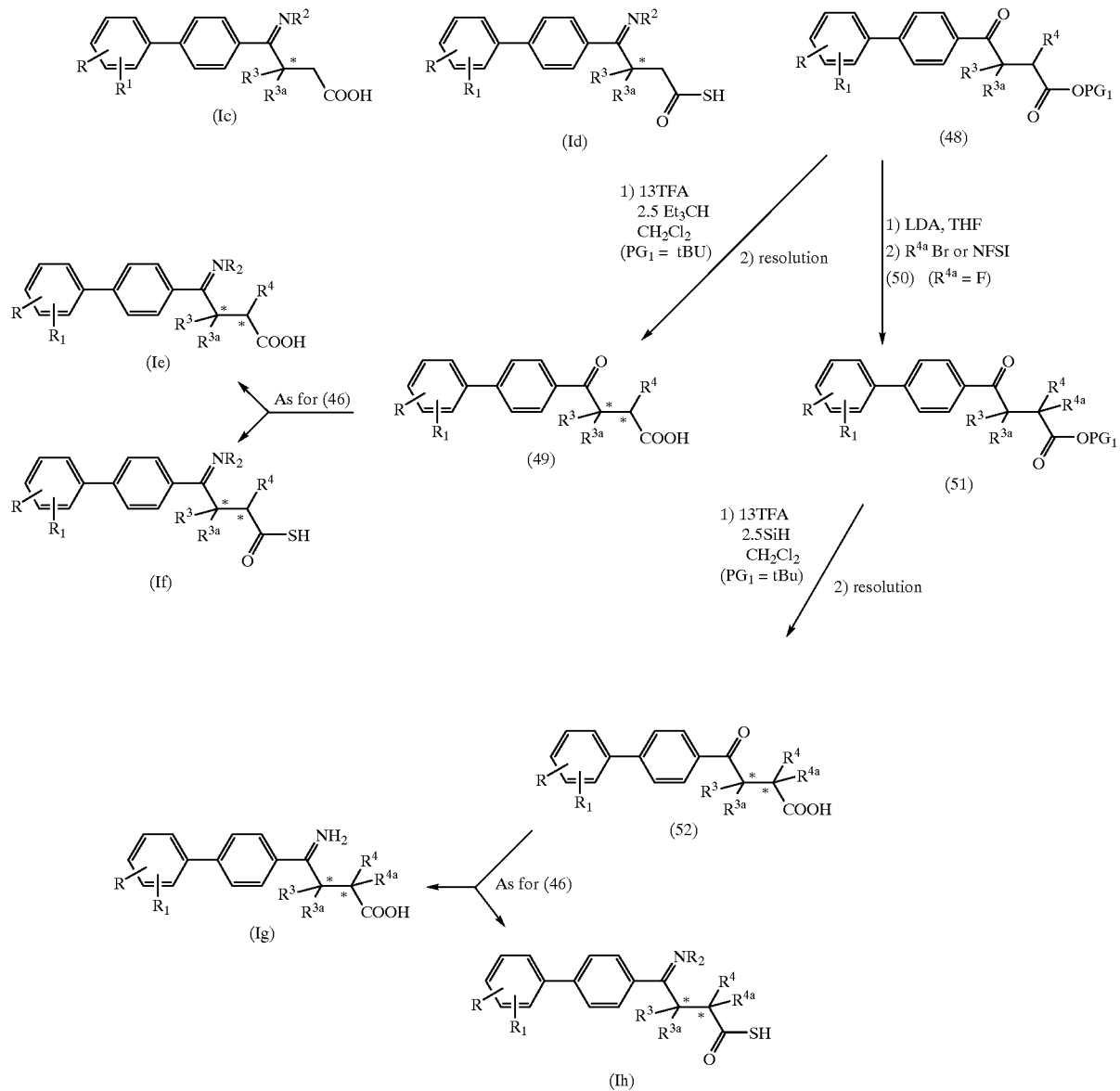

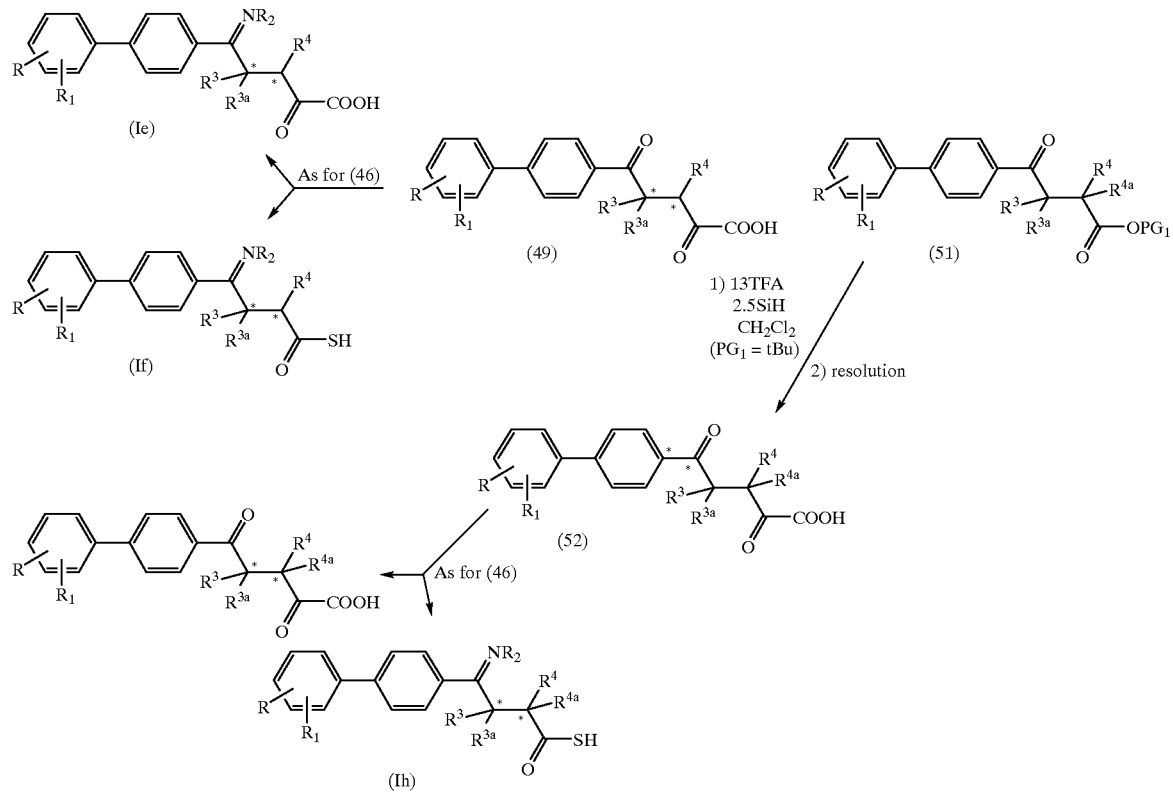

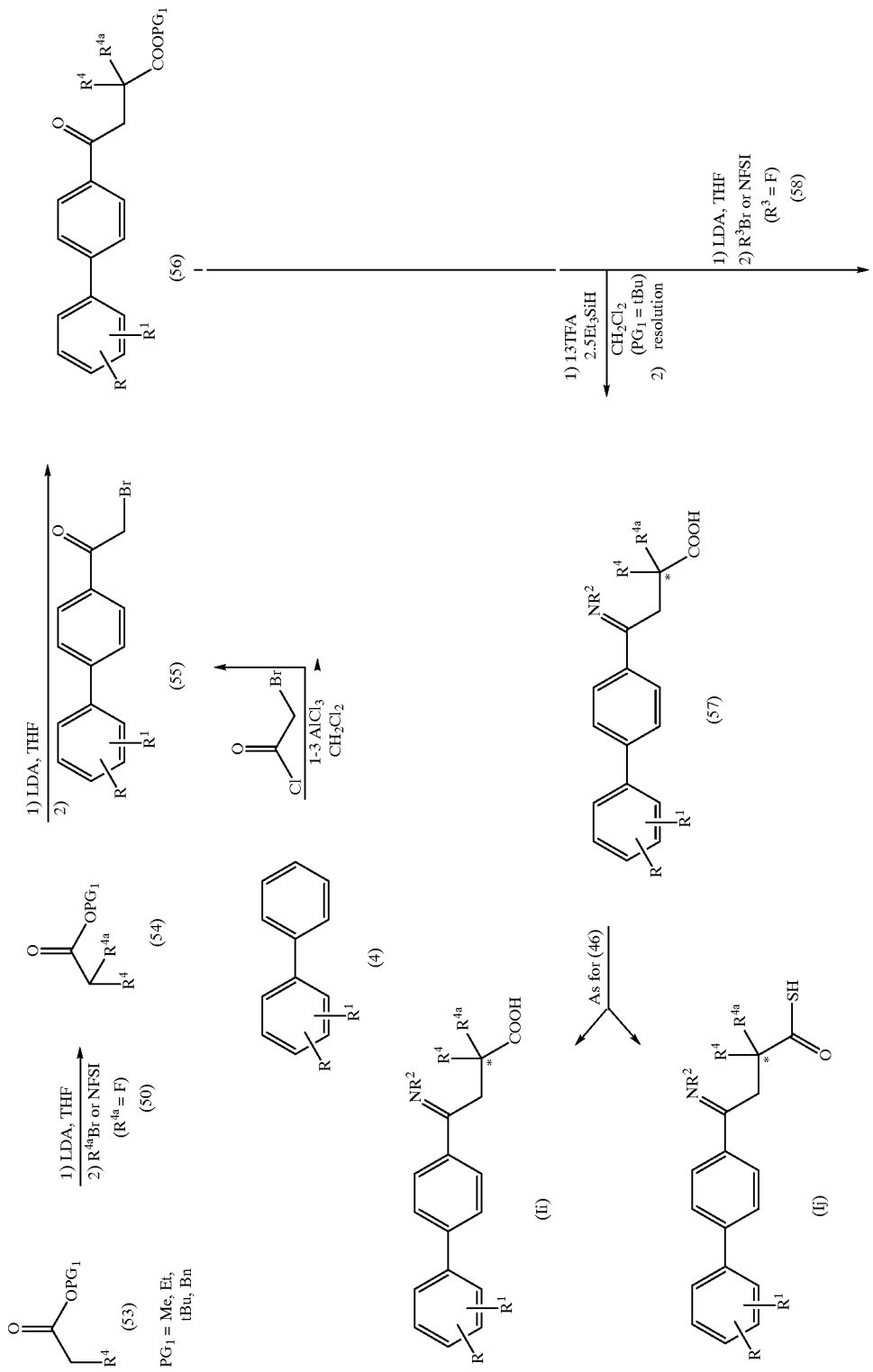

-continued
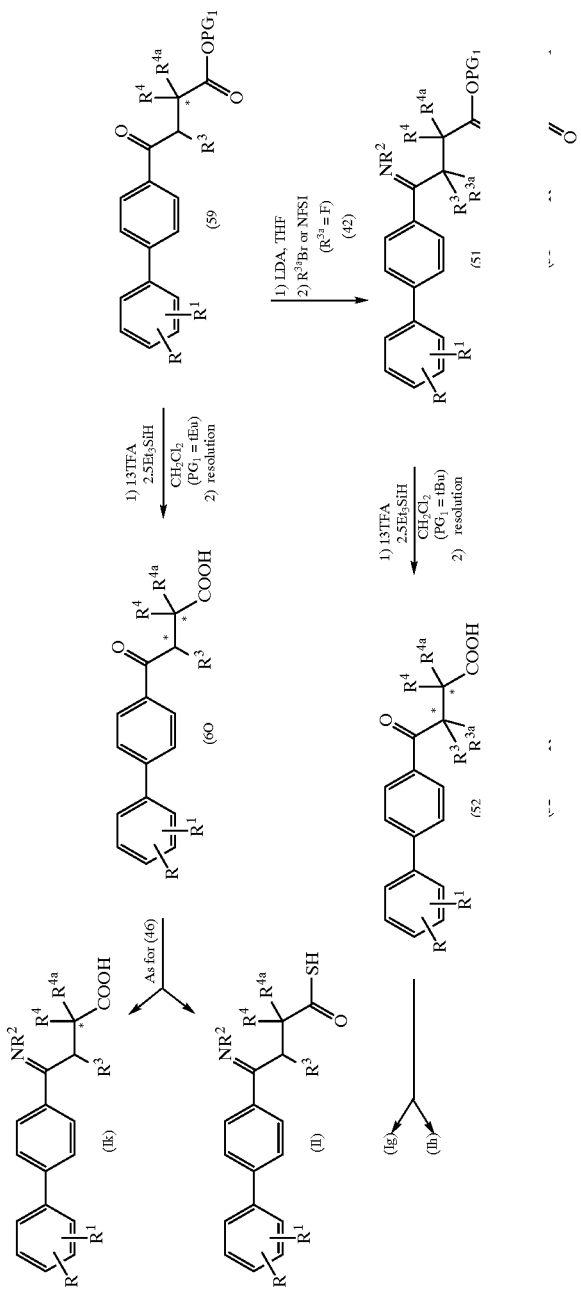

SCHEME 8
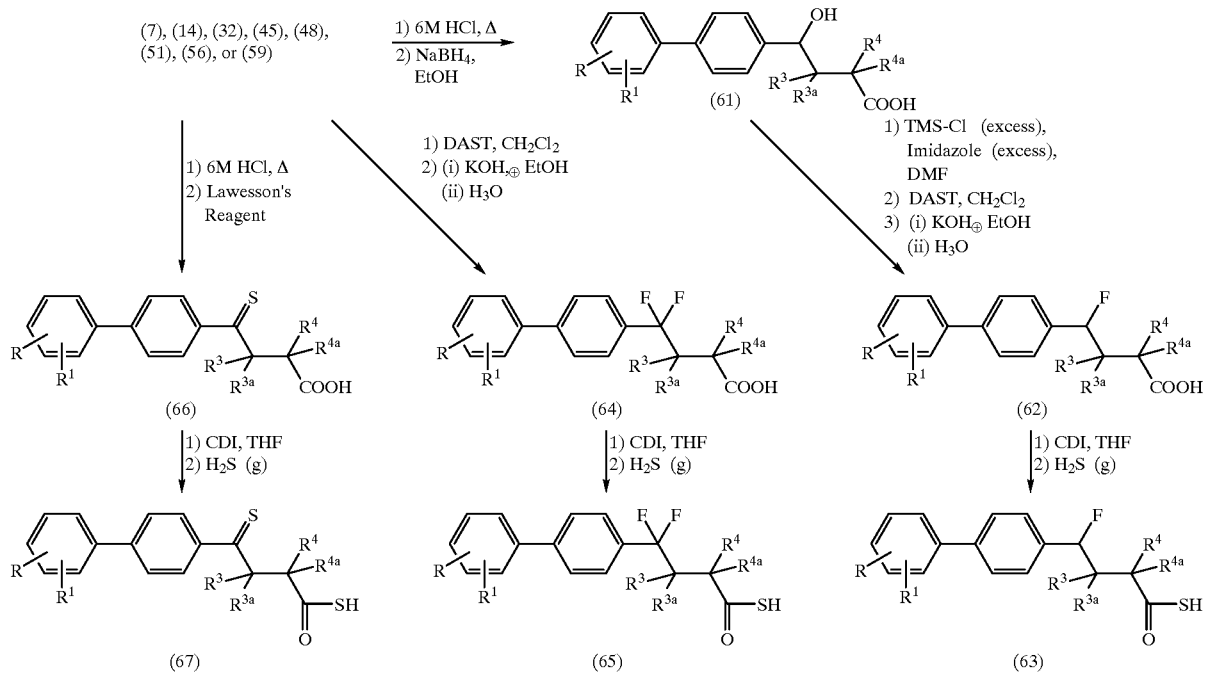
SCHEME 9
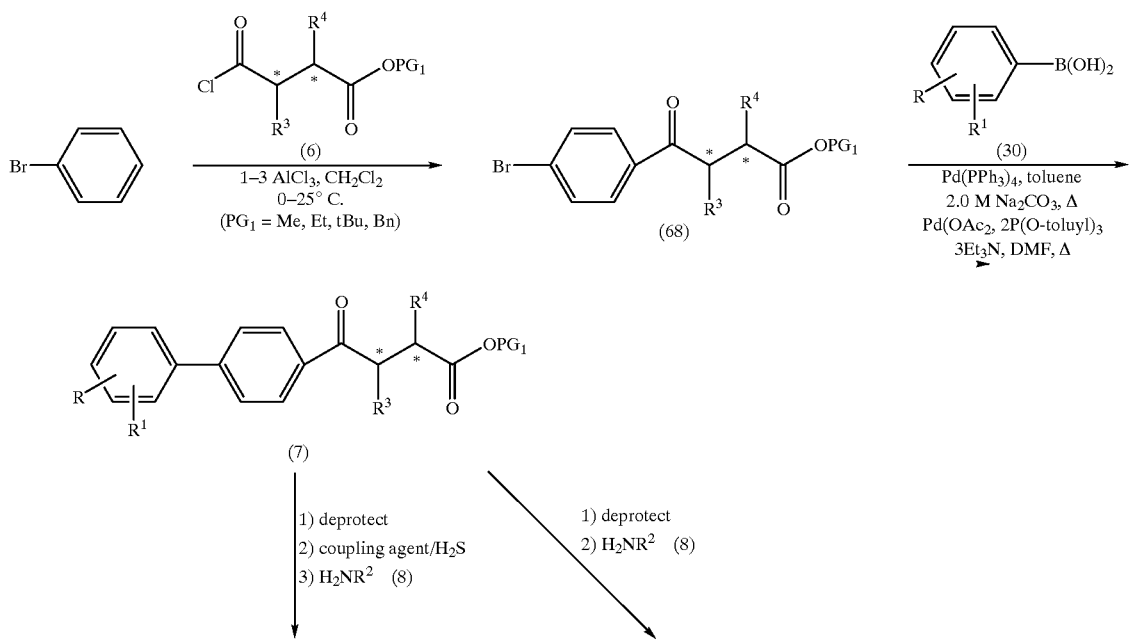

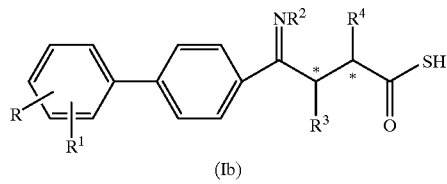
(Ib)

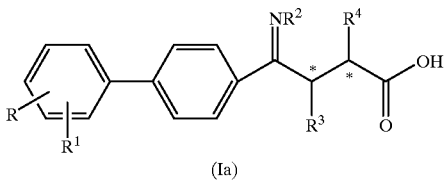
(Ia)

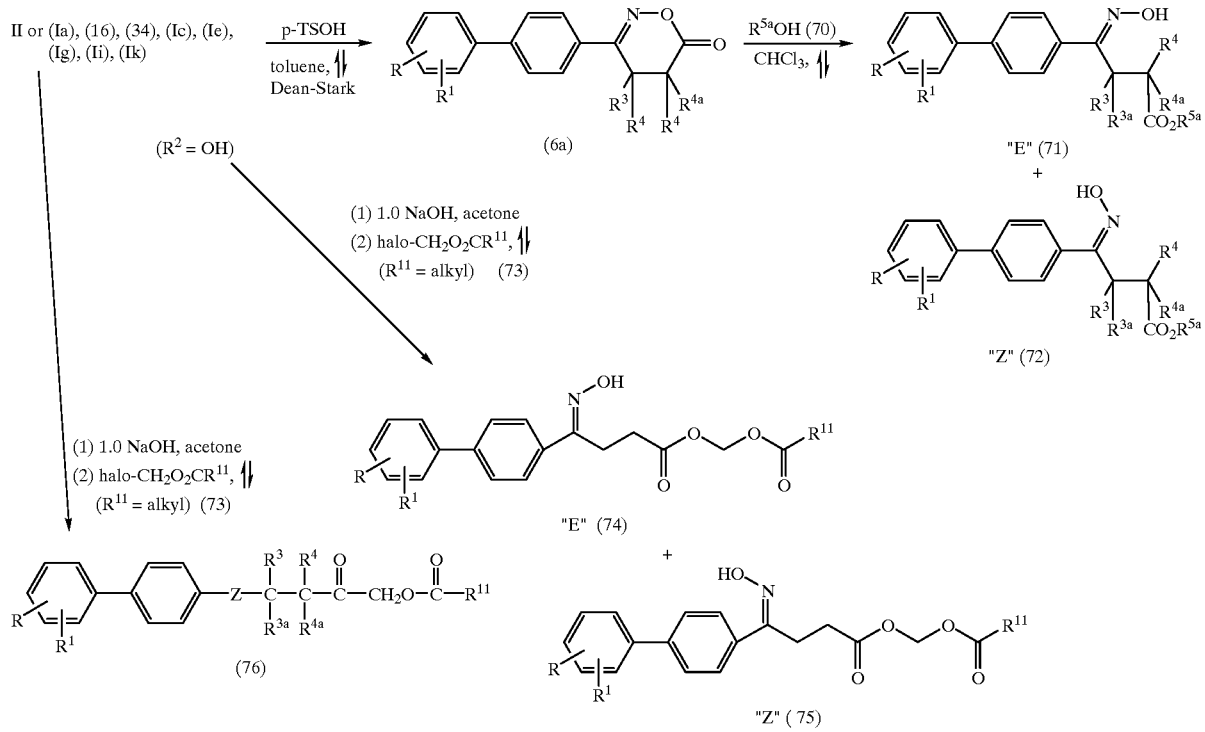

SCHEME 10

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intrapertioneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or Formula II or a corresponding pharmaceutically acceptable salt of a compound of Formula I or Formula II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 to 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, treatment of burns, decubital ulcers, wound healing, cancer, inflammation, pain, arthritis, or other autoimmune or inflammatory disorders dependent upon tissue invasion by leukocytes, or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, priori diseases, myasthenia gravis, and Duchenne's muscular dystrophy. The compounds utilized in the pharmaceutical methods of the invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

4-(4'-Chloro-biphenyl-4-yl)-4-yl)-4-hydroxyimino-butyric acid

Step (a) Preparation of 4-(4'-Chloro-biphenyl-4-yl)-4-oxo-butyric acid

A suspension of 4-chlorobiphenyl (9.43 g, 0.0500 mol), succinic anhydride (5.50 g, 0.0550 mol), and anhydrous aluminum chloride (14.8 g, 0.111 mol) in nitrobenzene (25 mL) at 5° C. under nitrogen was stirred 4 hours, then allowed to warm to room temperature. After 3 days, the mixture was heated at 95° C. to 120° C. for 1 hour, cooled to 5° C., and quenched with a mixture of ice (15 g), water (8 mL), and concentrated hydrochloric acid (HCl) solution (8 mL). Additional water (150 mL) was added, followed by ethyl acetate. The ethyl acetate layer was washed with 0.2 M HCl and extracted with saturated aqueous sodium bicarbonate solution. The bicarbonate layer was rotary evaporated briefly to remove residual ethyl acetate, then acidified by the dropwise addition of concentrated HCl solution. The resulting tan precipitate was filtered off, washed with 0.2 M HCl, and air dried. The solids were dissolved in hot toluene/acetone, and the solution was decolorized with activated carbon, and filtered hot through celite. The filtrate was concentrated, and the resulting crystals were filtered, washed, and dried in vacuo to give 1.96 g of 4-(4'-chloro-biphenyl-4-yl)-4-oxo-butyric acid as pale yellow plates; mp 184–185° C.

Step (b) Preparation of 4-(4'-Chloro-biphenyl-4-yl)-4-hydroxyimino-butyric acid

A mixture of 4-(4'-chloro-biphenyl-4-yl)-4-oxo-butyric acid (9.13 g, 0.0316 mol), hydroxylamine hydrochloride (2.64 g, 0.0380 mol), and sodium carbonate (4.04 g, 0.0381 mol) in absolute ethanol was refluxed under nitrogen for 13.5 hours and allowed to cool. The resulting suspension was filtered, and the filter cake was washed with ethanol followed by diethyl ether. The filter cake was dried under house vacuum to give a white solid. The solid was dissolved in methanol (450 mL), and the cloudy solution was filtered to remove fines. The filtrate was stirred while one equivalent of 1 M HCl was added dropwise followed by dropwise addition of deionized water (200 mL). The mixture was gently rotary evaporated (bath temperature=40° C.) to a volume of 150 mL. The solids that precipitated were chilled at 5° C. for 10 minutes and filtered. The filter cake was washed with water and dried in vacuo to give 6.82 g of 4-(4'-chloro-biphenyl-4-yl)-4-hydroxyimino-butyric acid as an off-white solid; mp 155–157° C.

EXAMPLE 2

4-(4'-Bromo-biphenyl-4-yl)-4-hydroxyimino-butyric acid

Step (a) Preparation of 4-(4'-Bromo-biphenyl-4-yl)-4-oxo-butyric acid, methyl ester To a stirred suspension of anhydrous aluminum chloride (3.45 g, 0.026 mol) in dichloromethane (20 mL) at 5° C. was added dropwise a solution of 4-bromobiphenyl (2.3 g, 0.010 mol) in dichloromethane (11 mL) followed by the dropwise addition of 3-carbomethoxypropionyl chloride (1.35 mL, 0.011 mol) in dichloromethane (15 mL), and the mixture stirred. After 2 hours at 5° C., the mixture was allowed to warm to room temperature. After 1 day, the reaction was cooled to 5° C. and quenched by the dropwise addition of water (50 mL). The layers were separated, and the organic layer washed with water and brine, dried (MgSO$_4$), and rotary evaporated. The residue was dissolved (CH$_2$Cl$_2$) and purified by column chromatography on silica gel, eluting with dichloromethane to give 2.68 g of 4-(4'-bromo-biphenyl-4-yl)-4-oxo-butyric acid, methyl ester as a white solid; mp 115.0–116.5° C.

Step (b) Preparation of 4-(4'-Bromo-biphenyl-4-yl)-4-oxo-butyric acid

A suspension of 4-(4'-bromo-biphenyl-4-yl)-4-oxo-butyric acid, methyl ester (2.636 g, 0.00759 mol) in 6 M HCl was refluxed for 214 hours and cooled to room temperature. The solids were filtered and washed with 1 M HCl. The filter cake was partitioned between ethyl acetate and 1 M sodium hydroxide. The aqueous layer was washed twice with ethyl acetate and filtered to remove particulates. The filtrate was rotary evaporated to remove residual ethyl acetate. The solution was stirred and acidified to pH 2 with concentrated HCl solution. The resulting precipitate was filtered, washed with water, and dried with house vacuum (air bleed) give 1.97 g of 4-(4'-bromo-biphenyl-4-yl)-4-oxo-butyric acid as a white solid; mp 198–200° C.

Step (c) Preparation of 4-(4'-Bromo-biphenyl-4-yl)-4-hydroxyimino-butyric acid

To a stirred suspension of 4-(4'-bromo-biphenyl-4-yl)-4-oxo-butyric acid (0.718 g, 0.00215 mol) and potassium carbonate (0.167 g, 0.00121 mol) in absolute ethanol (15 mL) was added a solution of hydroxylamine hydrochloride (0.180 g, 0.00259 mol) in water (3 mL), and the mixture stirred at room temperature for 6 days. The mixture was rotary evaporated. The residue was dissolved in methanol, silica gel (10 g) was added, and the mixture rotary evaporated to dryness. The powder was purified by chromatography on silica gel, eluting with dichloromethane-methanol (20:1) to give 0.499 g of 4-(4'-bromo-biphenyl-4-yl)-4-hydroxyimino-butyric acid as a white solid; mp 175–176° C.

EXAMPLE 3

4-(4'-Chloro-biphenyl-4-yl)-4-(dimethylhydrazono)-butyric acid

A stirred suspension of 4-(4'-chloro-biphenyl-4-yl)-4-oxo-butyric acid (0.578 g, 0.00200 mol) in a solution of dimethylhydrazine (0.46 mL, 0.0061 mol) in absolute ethanol (6 mL) was refluxed under nitrogen for 2.4 hours and allowed to cool. The volatiles were rotary evaporated, and the residue dissolved (CH$_2$Cl$_2$) and purified by column chromatography on silica gel, eluting with dichloromethane-methanol (24:1) to give 0-.33 g of 4-(4'-chloro-biphenyl-4-yl)-4-(dimethylhydroazono)-butyric acid as a yellow solid; mp 158–160° C.

EXAMPLE 4

4-(4'-Fluoro-biphenyl-4-yl)-4-hydroxyimino-butyric acid

Step (a) Preparation of 4-(4'-Fluoro-biphenyl-4-yl)-4-oxo-butyric acid, methyl ester To a stirred suspension of anhydrous aluminum chloride (9.64 g, 0.723 mol) in dichloromethane (90 mL) at 5° C. was added dropwise a solution of 4-fluorobiphenyl (4.97 g, 0.0289 mol) in dichloromethane (40 mL) followed by the dropwise addition of a solution of 3-carbomethoxypropionyl chloride (3.94 mL, 0.032 mol) in dichloromethane (30 mL), and the mixture stirred. After 2 hours at 5° C., the mixture was allowed to warm to room temperature. After 1 day, the reaction was cooled to 5° C. and quenched by the dropwise addition of water (160 mL). The layers were separated, and the organic layer washed with brine, dried (Na$_2$SO$_4$), and rotary evaporated. The residue was recrystallized from methanol (300 mL) to give 6.17 g of 4-(4'-fluoro-biphenyl-4-yl)-4-oxo-butyric acid, methyl ester as a pale yellow solid; mp 131.5–133.0° C.

Step (b) Preparation of 4-(4'-Fluoro-biphenyl-4-yl)-4-oxo-butyric acid

A suspension of 4-(4'-fluoro-biphenyl-4-yl)-4-oxo-butyric acid, methyl ester (6.08 g, 0.0212 mol) in 6 M hydrochloric acid was refluxed for 22 hours and cooled to room temperature. The solids were filtered and washed with 0.1 M hydrochloric acid. The filter cake was dried under house vacuum (air bleed) to give 5.72 g of 4-(4'-fluoro-biphenyl-4-yl)-4-oxo-butyric acid as a peach colored solid; mp 173.5–175.5° C.

Step (c) Preparation of 4-(4'-Fluoro-biphenyl-4-yl)-4-hydroxyimino-butyric acid

A stirred mixture of 4-(4'-fluoro-biphenyl-4-yl)-4-oxo-butyric acid (2.72 g, 0.0100 mol), hydroxylamine hydrochloride (0.848 g, 0.0122 mol) and sodium carbonate (1.304 g, 0.0123 mol) in absolute ethanol (60 mL) was refluxed for 22 hours and allowed to cool. The solids were filtered, washed with additional ethanol, and allowed to air dry overnight. The solids were dissolve din methanol-water, and the solution acidified with 1.0 M hydrochloric acid (10 mL, 0.010 mol HCl). The mixture was concentrated to approximately 30 mL on a rotary evaporator, and the resulting precipitate filtered and dried in vacuo to give 2.66 g of 4-(4'-fluoro-biphenyl-4-yl)-4-hydroxyimino-butyric acid as a pale yellow solid; mp 152–153° C.

EXAMPLE 5

($\approx$)-4-(4'-Chloro-biphenyl-4-yl)-4-hydroxy-butyric acid

To a stirred suspension of sodium borohydride (0.0376 g, 0.00099 mol) in absolute ethanol under nitrogen at room temperature was added in one portion 4-(4'-chloro-biphenyl-4-yl)-4-oxo-butyric acid (0.576 g, 0.00199 mol), and the mixture stirred for 4 hours. Additional sodium borohydride (0.013 g, 0.00034 mol) was added, and the mixture stirred for 18 hours. Additional sodium borohydride (0.0144 g, 0.000381 mol) was added and the mixture stirred for 5 hours. Total reaction time was 27 hours. The reaction was quenched with acetone-water and partitioned between 1 M hydrochloric acid and dichloromethane. The organic layer was washed with brine, dried (Na$_2$DO$_4$), and rotary evaporated. The residue was purified by chromatography on silica gel using dichloromethane-methanol (19:1, 1.3 L; 15.1, 1.3 L) to give 0.101 g of ($\pm$)-4-(4'-chloro-biphenyl-4-yl)-4-hydroxy-butyric acid as a white solid; mp 133.5–135.0° C.

EXAMPLE 6

4-(4'-Bromo-2'-fluoro-biphenyl-4-yl)-4-hydroxyimino-butyric acid

Step (a) Preparation of 4-(4'-Bromo-2'-fluoro-biphenyl-4-yl)-4-oxo-butyric acid, methyl ester To a stirred suspension of anhydrous aluminum chloride (3.35 g, 0.0251 mol) in dichloromethane (30 mL) at 5° C. under nitrogen was added dropwise a solution of 4-bromo-2-fluoro-biphenyl (2.512 g, 0.0100 mol) in dichloromethane (17 mL) followed by a solution of 3-carbomethoxypropionyl chloride (1.34 mL, 0.0109 mol) in dichloromethane (16 mL), and the mixture stirred. After 2 hours at 5° C., the mixture was allowed to warm to room temperature and stirred for 20 hours. The reaction was recooled to 5° C. and quenched by the dropwise addition of water (60 mL). The organic layer was washed with water, saturated sodium bicarbonate, brine, and dried (Na$_2$SO$_4$). The organics were rotary evaporated, and the residue was purified by chromatography on silica gel, eluting with chloroform to give 3.15 g of 4-(4'-bromo-2'-fluoro-biphenyl-4-yl)-4-oxo-butyric acid, methyl ester as a pale yellow solid; mp 94–95° C.

Step (b) Preparation of 4-(4'-Bromo-2'-fluoro-biphenyl-4-yl)-4-oxo-butyric acid

A suspension of 4-(4'-bromo-2'-fluoro-biphenyl-4-yl)-4-oxo-butyric acid, methyl ester (2.94 g, 0.00805 mol) in 6 M hydrochloric acid was refluxed for 23 hours and allowed to cool. The solids were filtered, washed with 0.1 M hydrochloric acid, and dried under house vacuum to give 2.76 g of 4-(4'-bromo-2'-fluoro-biphenyl-4-yl)-4-oxo-butyric acid as a pale yellow solid; mp 145–147° C.

Step (c) Preparation of 4-(4'-Bromo-2'-fluoro-biphenyl-4-yl)-4-hydroxyimino-butyric acid In a manner similar to that described for Example 4, Step (c), 4-(4'-bromo-2'-fluoro-biphenyl-4-yl)-4-oxo-butyric acid (1.05 g, 0.00300 mol) was allowed to react with hydroxylamine hydrochloride (0.256 g, 0.00368 mol) to give 1.00 g of 4-(4'-bromo-2'-fluoro-biphenyl-4-yl)-4-hydroxyimino-butyric acid as a white solid; mp 163–164° C.

EXAMPLE 7

(±)-4-(4'-Chloro-biphenyl-4-yl)-3-fluoro-4-oxo-butyric acid

To a stirred solution of diisopropylamine (0.295 mL, 0.0021 mol) in anhydrous tetrahydrofuran (10 mL) at room temperature under nitrogen was added in portions a 2.1 M solution of n-butyl lithium in hexanes (1.0 mL, 0.0021 mol), and the mixture cooled to −78° C. To a solution was added a solution of 4-(4'-chloro-biphenyl-4-yl)-4-oxo-butyric acid (0.288 g, 0.000997 mol) in THF (10 mL), and the mixture stirred for 1 hour. To the yellow solution was added dropwise a solution of N-fluorodibenzenesulfonamide (NFSI, 0.346 g, 0.00110 mol) in THF (10 mL), and the mixture stirred for 2 hours at −78° C. The mixture was allowed to warm to room temperature and stirred for 16 hours. The reaction was quenched with 1 M hydrochloric acid (1.1 mL, 0.0011 mol HCl), and the mixture was rotary evaporated to dryness. The residue was passed through a column of silica gel, eluting with dichloromethane-methanol (10:1 then 9:1) to give a gum. The gum was dissolved in methanol and acidified with additional 1 M hydrochloric acid (3.4 mL, 0.0034 mol HCl). The volatiles were rotary evaporated, and the resulting suspension was filtered. The filter cake was purified by chromatography on silica gel, eluting with dichloromethane-methanol (14:1) to give 0.030 g of (±)-4-(4'-chloro-biphenyl-4-yl)-3-fluoro-4-oxo-butyric acid as a white solid: mp 170–173° C.

EXAMPLE 8

4-(4'-Chloro-biphenyl-4-yl)-4-methoxyimino-butyric acid, sodium salt

A stirred suspension of 4-(4'-chloro-biphenyl-4-yl)-4-oxo-butyric acid (0.290 g, 0.00100 mol, O-methyl-hydroxylamine hydrochloride (0.106 g, 0.00127 mol) and sodium carbonate (0.1307 g, 0.00123 mol) in absolute ethanol (5 mL) was refluxed for 24 hours under nitrogen and allowed to cool. Volatiles were rotary evaporated, and the residue stirred in deionized water (10 mL). The solids were filtered, washed with additional water and dried in vacuo to give 4-(4'-chloro-biphenyl-4-yl)-4-methoxyimino-butyric acid, sodium salt as an off-white solid; mp 234–238° C.

EXAMPLE 9

4-(4'-Chloro-biphenyl-4-yl)-4-methoxyimino-butyric acid

A portion of 4-(4'-chloro-biphenyl-4-yl)-4-methoxyimino-butyric acid, sodium salt (0.23 g, 0.00068 mol) was partitioned between 0.1 M aqueous hydrochloric acid (10 mL) and tetrahydrofuran-dichloromethane (50/50 v/v). The organic layer was dried (Na$_2$SO$_4$) and rotary evaporated to give a pale yellow solid. The solid was crystallized from 2-propanol to give 0.143 g of 4-(4'-chloro-biphenyl-4-yl)-4-methoxyimino-butyric acid as a pale yellow solid; mp 183–186° C.

EXAMPLE 10

4-(4'-Chloro-2'-fluoro-biphenyl-4-yl)-4-hydroxyimino-butyric acid

Step (a) Preparation of 4-Chloro-2-fluoro-biphenyl

To a stirred solution of 4-chloro-2-fluoro-aniline (1.0 mL, 0.0090 mol) in benzene (50 mL) at room temperature under nitrogen was added in one portion neat iso-amyl nitrite (1.7 mL, 0.014 mol), and the mixture was slowly heated until gas evolution was observed (~70° C.). The heat source was removed and the solution allowed to cool. After 10 minutes at room temperature, the mixture was heated to reflux, refluxed 2 hours and cooled. The solution was rotary evaporated to ~3 mL and filtered through silica gel (100 g), eluting with hexanes. Fractions containing product were rotary evaporated, and the residue was rechromatographed on silica gel (50 g) eluting with n-hexane (20×50 mL) followed by n-hexane-diethyl ether (9:1, 10×50 mL) to give 0.875 g of 4-chloro-2-fluoro-biphenyl as a clear colorless oil; proton nuclear magnetic resonance spectroscopy ($^1$H-NMR) (CDCl$_3$): δ 7.36–7.53 (m, 6H), 7.18–7.22 (m, 2H).

Step (b) Preparation of 4-(4'-Chloro-2'-fluoro-biphenyl-4-yl)-4-oxo-butyric acid, methyl ester To a stirred suspension of anhydrous aluminum chloride (1.451 g, 0.0109 mol) in dichloromethane (20 mL) under nitrogen at 5° C. was added dropwise a solution of 4-chloro-2-fluorobiphenyl (0.858 g, 0.00415 mol) in dichloromethane (13 mL) over 10 minutes followed by the dropwise addition of 3-carbomethoxypropionyl chloride (0.57 mL, 0.0046 mol) in dichloromethane (13 mL) over 25 minutes. The resulting mixture was stirred for 2.5 hours then allowed to warm slowly to room temperature. Stirred for 3 days, for convenience. Then the mixture was recooled and quenched with the dropwise addition of water (145 mL). The organic layer was washed with water, aqueous sodium bicarbonate, brine, and dried (MgSO$_4$). The mixture was rotary evaporated to give 1.25 g of 4-(4'-chloro-2'-fluoro-biphenyl-4-yl)-4-oxo-butyric acid, methyl ester as a pale yellow solid: mp 90.5–92.5° C.

Step (c) Preparation of 4-(4'-Chloro-2'-fluoro-biphenyl-4-yl)-4-oxo-butyric acid In a manner similar to Example 4, Step (b), 4-(4'-chloro-2'-fluoro-biphenyl-4-yl)-4-oxo-butyric acid, methyl ester (1.39 g, 0.00433 mol) was refluxed in 6 M hydrochloric acid to give 1.22 g of 4-(4'-chloro-2'-fluoro-biphenyl-4-yl)-4-oxo-butyric acid as a light purple solid; mp 127–129° C.

Step (d) Preparation of 4-(4'-Chloro-2'-fluoro-biphenyl-4-yl)-4-hydroxyimino-butyric acid In a manner similar to Example 4, Step (c), 4-(4'-chloro-2'-fluoro-biphenyl-4-yl)-4-oxo-butyric acid (1.100 g, 0.00359 mol) was allowed to react with hydroxylamine hydrochloride (0.300 g, 0.00432 mol) in the presence of sodium carbonate (0.458 g, 0.00432 mol) in absolute ethanol (20 mL) to give 0.989 g of 4-(4'-chloro-2'-fluoro-biphenyl-4-yl)-4-hydroxyimino-butyric acid as an off-white solid; mp 147.5–149.5° C.

EXAMPLE 11

4-(2'-Fluoro-biphenyl-4-yl)-4-hydroxyimino-butyric acid

Step (a) Preparation of 4-(2'-Fluoro-biphenyl-4-yl)-4-oxo-butyric acid, methyl ester In a manner similar to Example 2, Step (a), 2-fluoro-biphenyl (6.284 g, 0.0365 mol) was allowed to react with 3-carbomethoxypropionyl chloride (4.95 mL, 0.0402 mol) in the presence of anhydrous aluminum chloride (10.7 g, 0.0802 mol) in dichloromethane to give, after chromatography on silica gel (456 g, 230–400 mesh), eluting with chloroform (15×450 mL), 7.36 g of 4-(2'-fluoro-biphenyl-4-yl)-4-oxo-butyric acid, methyl ester as a pale yellow solid: mp 75.5–77.5° C.

Step (b) Preparation of 4-(2'-Fluoro-biphenyl-4-yl)-4-oxo-butyric acid

To a stirred solution of 4-(2'-fluoro-biphenyl-4-yl)-4-oxo-butyric acid, methyl ester (7.17 g, 0.0250 mol) in tetrahydrofuran (60 mL) at room temperature was added a solution of sodium hydroxide (1.04 g, 0.026 mol) in methanol (60 mL), and the mixture was stirred for 23 hours. To the reaction was added 1.0 M aqueous sodium hydroxide (10 mL), and the mixture was stirred for an additional 24 hours. The mixture was rotary evaporated, and the residue was partitioned between water and chloroform. The aqueous layer was washed with chloroform (3×) and acidified with concentrated hydrochloric acid to pH=3. The resulting solids were filtered, washed with dilute aqueous hydrochloric acid (pH=3), and dried under house vacuum (air bleed) to give 6.51 g of 4-(2'-fluoro-biphenyl-4-yl)-4-oxo-butyric acid as a pale yellow solid; mp 148–153° C.

Step (c) Preparation of 4-(2'-Fluoro-biphenyl-4-yl)-4-hydroxyimino-butyric acid

In a manner similar to Example 4, Step (c), 4-(2'-fluoro-biphenyl-4-yl)-4-oxo-butyric acid (1.634 g, 0.006001 mol) was allowed to react with hydroxylamine hydrochloride (0.500 g, 0.00720 mol) in the presence of sodium carbonate (0.763 g, 0.00720 mol) in absolute ethanol to give 1.434 g of 4-(2'-fluoro-biphenyl-4-yl)-4-hydroxyimino-butyric acid as a pale yellow solid; mp 150.0–151.5° C.

EXAMPLE 12

4-Hydroxyimino-4-(4'-methyl-biphenyl-4-yl)-butyric acid

Step (a) Preparation of 4-(4-Bromo-phenyl)-4-oxo-butyric acid, methyl ester

In a manner similar to Example 2, Step (a), bromobenzene (10.0 mL, 0.0950 mol) was allowed to react with 3-carbomethoxypropionyl chloride (12.9 mL, 0.105 mol) in the presence of aluminum chloride (26.9 g, 0.0202 mol) in dichloromethane to give, after chromatography on silica gel (435 g, 230–400 mesh), eluting with hexanes-acetone (9:1, 10×400 mL; 8:1, 7×400 mL), 21.2 g of 4-(4-bromo-phenyl)-4-oxo-butyric acid, methyl ester as an off-white solid; mp 49–51° C.

Step (b) Preparation of 4-(4'-Methyl-biphenyl-4-yl)-4-oxo-butyric acid, methyl ester To a stirred mixture of (4-methylphenyl)boronic acid (0.818 g, 0.00602 mol) and 4-(4-bromo-phenyl)-4-oxo-butyric acid, methyl ester (1.3556 g, 0.00500 mol) in toluene (10 mL) was added tetrakis(triphenylphosphine)-palladium (0) (0.173 g, 0.000150 mol) and 2.0 M aqueous sodium carbonate (5.0 mL, 0.010 mol), and the mixture was heated at reflux under nitrogen for 12 hours and allowed to cool. The mixture was diluted with toluene and dichloromethane (10 mL/10 mL), and filtered through a pad of Celite. The Celite was washed with additional toluene and dichloromethane. Filtrate and washings were combined and washed with 2.0 M aqueous sodium carbonate, brine, 3% aqueous ammonium hydroxide, water, and brine. The organics were dried ($Na_2SO_4$) and rotary evaporated. The residue was dissolved in chloroform and purified by column chromatography on silica gel (144 g, 230–400 mesh), eluting with hexanes-acetone (6:1, 17×125 mL) to give 0.98 g of 4-(4'-methyl-biphenyl-4-yl)-4-oxo-butyric acid, methyl ester as a white solid; mp 121–122° C.

Step (c) Preparation of 4-(4'-Methyl-biphenyl-4-yl)-4-oxo-butyric acid

In a manner similar to Example 4, Step (b), 4-(4'-methyl-biphenyl-4-yl)-4-oxo-butyric acid, methyl ester (1.21 g, 0.0043 mol) was refluxed in 6 M aqueous hydrochloric acid to give 1.12 g of 4-(4'-methyl-biphenyl-4-yl)-4-oxo-butyric acid as an off-white solid; mp 183–186° C.

Step (d) Preparation of 4-Hydroxyimino-4-(4'-methyl-biphenyl-4-yl)-butyric acid

In a manner similar to Example 4, Step (c), 4-(4'-methyl-biphenyl-4-yl)-4-oxo-butyric acid (1.052 g, 0.003922 mol) was allowed to react with hydroxylamine hydrochloride (0.3245 g, 0.00467 mol) in the presence of sodium carbonate (0.498 g, 0.00470 mol) in absolute ethanol to give 1.006 g of 4-hydroxyimino-4-(4'-methyl-biphenyl-4-yl)-butyric acid as a white solid; mp 176.5–177.5° C.

EXAMPLE 13

4-Hydroxyimino-4-(4'-methoxy-biphenyl-4-yl)-butyric acid

Step (a) Preparation of 4-(4'-Methoxy-biphenyl-4-yl)-4-oxo-butyric acid, methyl ester In a manner similar to Example 12, Step (b), (4-methoxyphenyl)boronic acid (0.913 g, 0.00601 mol) was allowed to react with 4-(4-bromo-phenyl)-4-oxo-butyric acid, methyl ester (1.356 g, 0.00500 mol) in the presence of tetrakis(triphenylphosphine)palladium(0) (0.173 g, 0.000150 mol) and 2.0 M aqueous sodium carbonate (5.0 mL, 0.010 mol) in toluene (10 mL) to give, after chromatography on silica gel (270 g, 230–400 mesh), eluting with dichloromethane (15×250 mL); dichloromethane-methanol (100:1, 19×225 mL; 50:1, 5×225 mL), 1.386 g of 4-(4'-methoxy-biphenyl-4-yl)-4-oxo-butyric acid, methyl ester as a white solid; mp 96.0–100.5° C.

Step (b) Preparation of 4-(4'-Methoxy-biphenyl-4-yl)-4-oxo-butyric acid

To a stirred suspension of 4-(4'-methoxy-biphenyl-4-yl)-4-oxo-butyric acid, methyl ester (1.342 g, 0.00450 mol) in methanol (15 mL) at room temperature was added 50/50 wt/wt aqueous sodium hydroxide (0.41 g, 0.0051 mol), and the mixture was stirred for 3 days, for convenience. To the mixture was added 1.0 M aqueous sodium hydroxide (0.45 mL, 0.00045 mol) and stirring was continued for 1 day. The mixture was rotary evaporated, and the residue was partitioned between dichloromethane-tetrahydrofuran (50/50 v/v) and 0.2 M aqueous hydrochloric acid. The organic layer was washed with brine and dried ($Na_2SO_4$). The mixture was rotary evaporated, and the residue was purified by chromatography on silica gel (154 g, 230–400 mesh), eluting with dichloromethane (7×225 mL); dichloromethane-methanol (19:1, 7×225 mL) to give 0.929 g of 4-(4'-methoxy-biphenyl-4-yl)-4-oxo-butyric acid as an off-white solid; mp 197–199° C.

Step (c) Preparation of 4-Hydroxyimino-4-(4'-methoxy-biphenyl-4-yl)-butyric acid In a manner similar to Example 4, Step (c), (4'-methoxy-biphenyl-4-yl)-4-oxo-butyric acid (1.08 g, 0.00380 mol) was allowed to react with hydroxylamine hydrochloride (0.316 g, 0.00455 mol) in the presence of sodium carbonate (0.485 g, 0.00458 mol) in absolute ethanol (20 mL) to give 0.983 g of 4-hydroxyimino-4-(4'-methoxy-biphenyl-4-yl)-butyric acid as a pale yellow solid; mp 157–160° C.

EXAMPLE 14

4-(4'-Cyano-biphenyl-4-yl)-4-hydroxyimino-butyric acid

Step (a) Preparation of 4-(4'-Cyano-biphenyl-4-yl)-4-oxo-butyric acid, methyl ester To a stirred solution of 4-bromobenzonitrile (1.807 g, 0.009929 mol) in anhydrous tetrahydrofuran (30 mL) at −85° C. under nitrogen was added dropwise over 15 minutes a 2.1 M solution of n-butyl lithium in hexanes (4.7 mL, 0.0099 mol), and the mixture was stirred. After 20 minutes, trimethylborate (1.0 mL, 0.0088 mol) was added in one portion, and the mixture was allowed to slowly warm. After 40 minutes, the reaction was quenched with 1 M aqueous hydrochloric acid (2.2 mL, 0.0022 mol) and stirred. Solids began crystallizing after 1 hour. The solids were filtered, washed with diethyl ether, and dried under house vacuum (air bleed, T=40° C.) to give 0.918 g of crude (4-cyano-phenyl)boronic acid. This material was used in the next reaction without further purification.

A stirred mixture of (4-cyano-phenyl)boronic acid (0.220 g, 0.00150 mol), 4-(4-bromo-phenyl)-4-oxo-butyric acid, methyl ester (0.2715 g, 0.00100 mol), triethylamine (0.418 mL, 0.0030 mol), tri(O-toluyl)phosphine (0.0191 g, 0.0000628 mol) and palladium(II)acetate (0.0067 g, 0.000030 mol) in dry dimethylformamide (4.0 mL) was heated at 105° C. under nitrogen for 2 hours and allowed to cool. For convenience, allowed to stand overnight. The mixture was diluted with diethyl ether, and the resulting suspension was filtered through Celite. The Celite and filtercake were washed with additional diethyl ether then dichloromethane. The filtrate and washings were combined and washed with 0.5 M aqueous hydrochloric acid, water, 3% aqueous ammonium hydroxide, water, and brine. The organics were dried ($Na_2SO_4$) and rotary evaporated. The residue was dissolved (chloroform) and chromatographed on silica gel (35 g, 230–400 mesh), eluting with hexanes-acetone (4:1, 30×30 mL) to give 0.172 g of 4-(4'-cyano-biphenyl-4-yl)-4-oxo-butyric acid, methyl ester as a pale yellow solid; mp 149–151° C.

Step (b) Preparation of 4-(4'-Cyano-biphenyl-4-yl)-4-oxo-butyric acid

To a stirred solution of 4-(4'-cyano-biphenyl-4-yl)-4-oxo-butyric acid, methyl ester (0.143 g, 0.000488 mol) in tetrahydrofuran at 15° C. was added in one portion a 1.0 M aqueous solution of sodium hydroxide (0.50 mL, 0.00050 mol), and the mixture was allowed to stir at room temperature for 18 hours. The THF was rotary evaporated, and the residue was partitioned between water and chloroform. The aqueous layer was washed with additional chloroform. The aqueous layer was acidified with 1.0 M aqueous hydrochloric acid (0.50 mL), and extracted with dichloromethane-tetrahydrofuran (50/50 v/v). The extract was washed with brine, dried ($Na_2SO_4$) and rotary evaporated. The residue was dried in vacuo to give 0.130 g of 4-(4'-cyano-biphenyl-4-yl)-4-oxo-butyric acid as a pale yellow solid; mp 191–193° C.

Step (c) Preparation of 4-(4'-Cyano-biphenyl-4-yl)-4-hydroxyimino-butyric acid

A stirred suspension of 4-(4'-cyano-biphenyl-4-yl)-4-oxo-butyric acid (0.7908 g, 0.002831 mol), hydroxylamine hydrochloride (0.2038 g, 0.00293 mol), sodium carbonate (0.3158 g, 0.00298 mol) in absolute ethanol (17 mL) was refluxed under nitrogen for 12 hours and allowed to cool. The mixture was allowed to stand for 2.5 days for convenience. Volatiles were rotary evaporated, and the residue was partitioned between dichloromethane-tetrahydrofuran (50/50 v/v) and 0.05 M aqueous hydrochloric acid (60 mL). The aqueous layer was extracted with additional organics. The extracts were combined, dried ($Na_2SO_4$) and rotary evaporated. The residue was dissolved/suspended in dichloromethane and chromatographed on silica gel (165 g, 230–400 mesh), eluting with dichloromethane-methanol (25:1, 30×125 mL; 15:1, 5×125 mL) to give 0.413 g of 4-(4'-cyano-biphenyl-4-yl)-4-hydroxyimino-butyric acid as an off-white solid; mp 157–159° C.

EXAMPLE 15

4-(3'-Fluoro-biphenyl-4-yl)-4-hydroxyimino-butyric acid

Step (a) Preparation of 4-(3'-Fluoro-biphenyl-4-yl)-4-oxo-butyric acid, methyl ester In a manner similar to Example 12, Step (b), (3-fluoro-phenyl)boronic acid (0.7698 g, 0.005502 mol) was allowed to react with 4-(4-bromo-phenyl)-4-oxo-butyric acid, methyl ester (1.356 g, 0.00500 mol) in the presence of tetrakis(triphenylphosphine)palladium(0) (0.173 g, 0.000150 mol) and 2.0 M aqueous sodium carbonate (5.0 mL, 0.010 mol) in toluene (10 mL) to give, after chromatography on silica gel (270 g, 230–400 mesh), eluting with chloroform (18×125 mL), 1.221 g of 4-(3'-fluoro-biphenyl-4-yl)-4-oxo-butyric acid, methyl ester as a white solid; mp 99–101° C.

Step (b) Preparation of 4-(3'-Fluoro-biphenyl-4-yl)-4-oxo-butyric acid

In a manner similar to Example 4, Step (b), 4-(3'-fluoro-biphenyl-4-yl)-4-oxo-butyric acid, methyl ester (1.0968 g, 0.00383 mol) was refluxed in 6 M aqueous hydrochloric acid (20 mL) to give 1.007 g of 4-(3'-fluoro-biphenyl-4-yl)-4-oxo-butyric acid as a pale orange solid; mp 153–155° C.

Step (c) Preparation of 4-(3'-Fluoro-biphenyl-4-yl)-4-hydroxyimino-butyric acid

In a manner similar to Example 4, Step (c), 4-(3'-fluoro-biphenyl-4-yl)-4-oxo-butyric acid (0.9258 g, 0.00340 mol) was allowed to react with hydroxylamine hydrochloride (0.284 g, 0.00409 mol) in the presence of sodium carbonate (0.434 g, 0.00409 mol) in absolute ethanol (19 mL) to give 4-(3'-fluoro-biphenyl-4-yl)-4-hydroxyimino-butyric acid as a pale gray solid; mp 155–157° C.

EXAMPLE 16

4-Hydroxyimino-4-(4'-trifluoromethyl-biphenyl-4-yl)-butyric acid

Step (a) Preparation of 4-Oxo-4-(4'-trifluoromethyl-biphenyl-4-yl)-butyric acid, methyl ester In a manner similar to Example 12, Step (b), (4-trifluoromethyl-phenyl)boronic acid (1.285 g, 0.00676 mol) was allowed to react with 4-(4'-bromo-phenyl)-4-oxo-butyric acid, methyl ester (1.356 g, 0.00500 mol) in the presence of tetrakis(triphenylphosphine)palladium(0) (0.173 g, 0.000150 mol) and 2.0 M aqueous sodium carbonate (5.0 mL, 0.010 mol) in toluene (10 mL) to give, after chromatography on silica gel (270 g, 230–400 mesh), eluting with chloroform to give 1.42 g of 4-oxo-4-(4'-trifluoromethyl-biphenyl-4-yl)-butyric acid, methyl ester as a white solid; mp 140–142° C.

Step (b) Preparation of 4-Oxo-4-(4'-trifluoromethyl-biphenyl-4-yl)-butyric acid

In a manner similar to Example 4, Step (b), 4-oxo-4-(4'-trifluoromethyl-biphenyl-4-yl)-butyric acid, methyl ester (1.34 g, 0.00398 mol) was refluxed in 6 M aqueous hydrochloric acid (24 mL) to give 1.27 g of 4-oxo-4-(4'-trifluoromethyl-biphenyl-4-yl)-butyric acid as an 80% pure solid. A portion (0.059 g) of the material was purified by chromatography on silica gel (7 g, 230–400 mesh), eluting with dichloromethane (15×10 mL); dichloromethane-methanol (15:1, 16×10 mL) to give 0.0476 g of pure 4-oxo-4-(4'-trifluoromethyl-biphenyl-4-yl)-butyric acid as an off-white solid; mp 172–174° C.

Step (c) Preparation of 4-Hydroxyimino-4-(4'-trifluoromethyl-biphenyl-4-yl)-butyric acid In a manner similar to Example 4, Step (c), 4-oxo-4-(4'-trifluoromethyl-biphenyl-4-yl)-butyric acid (1.20 g, 0.00372 mol) was allowed to react with hydroxylamine hydrochloride (0.3115 g, 0.00448 mol) in the presence of sodium carbonate (0.4768 g, 0.00450 mol) in absolute ethanol (20 mL) to give 0.764 g of 4-hydroxyimino-4-(4'-trifluoromethyl-biphenyl-4-yl)-butyric acid as a white solid; mp 134–136° C.

EXAMPLE 17

4-Hydroxyimino-4-(4'-methylsulfanyl-biphenyl-4-yl)-butyric acid

Step (a) Preparation of 4-(4'-Methylsulfanyl-biphenyl-4-yl)-4-oxo-butyric acid, methyl ester In a manner similar to Example 12, Step (b), 4-(methylsulfanyl-phenyl)boronic acid (0.930 g, 0.00553 mol) was allowed to react with 4-(4-bromo-phenyl)-4-oxo-butyric acid, methyl ester (1.356 g, 0.00500 mol) in the presence of tetrakis(triphenylphosphine)palladium(0) (0.162 g, 0.000140 mol) and 2.0 M aqueous sodium carbonate (5.0 mL, 0.010 mol) in toluene (10 mL) to give, after chromatography on silica gel (168 g, 230–400 mesh), eluting with hexanes-acetone (11:1, 20×125 mL; 9:1, 10×125 mL; 6:1, 30×125 mL), 0.405 g of 4-(4'-methylsulfanyl-biphenyl-4-yl)-4-oxo-butyric acid, methyl ester as a white solid; mp 137–140° C.

Step (b) Preparation of 4-Hydroxyimino-4-(4'-methylsulfanyl-biphenyl-4-yl)-butyric acid A mixture of 4-(4'-methylsulfanyl-biphenyl-4-yl)-4-oxo-butyric acid, methyl ester (0.3742 g, 0.001190 mol) and 1.0 M aqueous sodium hydroxide (1.3 mL, 0.0013 mol) in tetrahydrofuran-methanol (5 mL/5 mL) was stirred at room temperature for 3 days. The volatiles were rotary evaporated, and the residue was suspended in water. The suspension was acidified with 1.0 M aqueous hydrochloric acid (1.4 mL, 0.0014 mol), and the mixture was extracted with tetrahydrofuran-dichloromethane (50/50 v/v). The organics were washed with brine, dried ($Na_2SO_4$) and rotary evaporated to give 0.34 g of crude 4-(4'-methylsulfanyl-biphenyl-4-yl)-4-oxo-butyric acid as an off-white solid. A portion of this material (0.3383 g, 0.0011 mol) was stirred with hydroxylamine hydrochloride (0.0931 g, 0.00134 mol) in the presence of sodium carbonate (0.1438 g, 0.001357 mol) in absolute ethanol (7 mL) at reflux for 20 hours and allowed to cool. The volatiles were rotary evaporated, and the residue was partitioned between dichloromethane-tetrahydrofuran (50/50, v/v) and 0.10 M aqueous hydrochloric acid (25 mL). The organics were washed with brine, dried ($Na_2SO_4$) and rotary evaporated. The residue was dissolved in tetrahydrofuran, silica gel (4.0 g) was added, and the mixture was rotary evaporated to dryness. The resulting powder was chromatographed on silica gel (48 g, 230–400 mesh), eluting with dichloromethane-diethyl ether (24:1, 13×50 mL); dichloromethane-methanol (24:1, 13×50 mL; 20:1, 10×50 mL) to give 0.0525 g of 4-hydroxyimino-4-(4'-methylsulfanyl-biphenyl-4-yl)-butyric acid as a white solid; mp 162–164° C.

EXAMPLE 18

3-(4'-Chloro-biphenyl-4-yl)-4,5-dihydro-6-oxo-6H-1,2-oxazine

A stirred suspension of 4-(4'-chloro-biphenyl-4-yl)-4-hydroxyimino-butyric acid (2.126 g, 0.00700 mol) and 4-methylphenyl)sulfonic acid monohydrate (0.067 g, 0.00035 mol) in toluene (22 mL) was heated under nitrogen at reflux over a Dean-Stark trap for 7 hours, and allowed to cool. The volatiles were rotary evaporated. The residue was dissolved/suspended in dichloromethane and chromatographed on silica gel (221 g, 230–400 mesh), eluting with dichloromethane (20×200 mL) to give 0.63 g of 3-(4'-chloro-biphenyl-4-yl)-4,5-dihydro-6-oxo-6H-1,2-oxazine as a light purple solid; mp 190–192° C.

EXAMPLE 19

4-(4'-Chloro-biphenyl-4-yl)-4-hydroxyimino-butyric acid, sodium salt monohydrate To a stirred solution/suspension of 4-(4'-chloro-biphenyl-4-yl)-4-hydroxyimino-butyric acid (3.22 g, 0.0101 mol) in methanol (35 mL) at room temperature was added a solution of sodium hydroxide (0.4062 g, 0.0102 mol) in water (6 mL), and the resulting suspension was stirred at 30° C. for 1 hour. The resulting suspension was rotary evaporated to give a white solid. The solid was dried in vacuo. A portion of the solid (1.059 g, 0.003105 mol) was crystallized from water (8.4 mL) after hot gravity filtration, and the crystals were dried in vacuo to give 0.856 g of 4-(4'-chloro-biphenyl-4-yl)-4-hydroxyimino-butyric acid, sodium salt monohydrate; mp 222–224° C.

EXAMPLE 20

4-(4'-Chloro-biphenyl-4-yl)-4-hydroxyimino-butyric acid, hemi calcium salt

To a stirred suspension of 4-(4'-chloro-biphenyl-4-yl)-4-hydroxyimino-butyric acid (0.4556 g, 0.00150 mol) in methanol (10 mL) at room temperature was added water (3.5 mL), and the mixture was heated to boiling. To the mixture was added dropwise a solution of calcium acetate monohydrate (0.1136 g, 0.000645 mol) in water (2.0 mL). This produced an immediate precipitate. After addition was complete, the mixture was heated for 5 minutes and allowed to cool. After 1 hour at room temperature, the solids were filtered off, washed with methanol, and dried in vacuo. The solids were suspended in boiling tetrahydrofuran (11 mL), water (5.5 mL) was added until a solution was obtained. The solution was gravity filtered hot, and the filtrate was allowed to cool. The solids that crystallized were filtered, washed with THF-$H_2O$, and dried in vacuo to give 0.1976 g of 4-(4'-chloro-biphenyl-4-yl)-4-hydroxyimino-butyric acid, hemi calcium salt; $^1$H-NMR (DMSO-$d_6$): δ 11.45 (br s, 0.95H), 10.65 (br s, 0.05H), 7.66–7.74 (m, 6H), 7.49 (d, 2H), 2.92 (t, 2H), 2.17 (t, 2H).

EXAMPLE 21

4-(4'-Chloro-biphenyl-4-yl)-4-hydroxyimino-butyric acid, procaine salt

A suspension of 4-(4'-chloro-biphenyl-4-yl)-4-hydroxyimino-butyric acid (1.0404 g, 0.003425 mol) and procaine (0.8022 g, 0.003395 mol) in deionized water (20 mL) was heated on a steam bath. After 30 minutes, methanol (15 mL) was added in portions until a cloudy solution was obtained. The mixture was allowed to cool. The solids that crystallized were filtered, washed with water, and dried in vacuo to give 1.693 g of 4-(4'-chloro-biphenyl-4-yl)-4-hydroxyimino-butyric acid, procaine salt; mp 148–150° C.

EXAMPLE 22

4-(4'-Chloro-biphenyl-4-yl)-4-hydroxyimino-butyric acid, hemi magnesium salt, dihydrate To a gently boiling solution of 4-(4'-chloro-biphenyl-4-yl)-4-hydroxyimino-butyric acid (0.4557 g, 0.001500 mol) in methanol (13.5 mL) was added dropwise water (1.6 mL) followed by the dropwise addition of a solution of magnesium acetate tetrahydrate (0.1600 g, 0.000746 mol) in water (3.2 mL). The resulting solution was allowed to cool. Crystallization began immediately. The mixture was allowed to slowly concentrate by evaporation over 2 days. The suspension was chilled for 4 hours, and the crystals were filtered and dried under house vacuum (air bleed, 40° C.) to give 0.4479 g of 4-(4'-chloro-biphenyl-4-yl)-4-hydroxyimino-butyric acid, hemi magnesium salt, dihydrate as a pale yellow solid; $^1$H-NMR (DMSO-$d_6$): δ 11.37 (br s, 0.95H), 10.8 (br s, 0.05H), 7.50–7.75 (m, 6H), 7.47 (d, 2H), 2.94 (m, 2H), 2.26 (m, 2H).

EXAMPLE 23

4-(4'-tert-Butyl-biphenyl-4-yl)-4-hydroxyimino-butyric acid

Step (a) Preparation of 4-(4'-tert-Butyl-biphenyl-4-yl)-4-oxo-butyric acid, methyl ester To a stirred solution of 4-tert-butyl-bromobenzene (21.3 g, 0.0999 mol) in THF (30 mL) at −78° C. under nitrogen was added dropwise a 2.1 M solution of n-butyl lithium in hexanes (45 mL, 0.095 mol), and the mixture was stirred for 1.5 hours. To the mixture was added dropwise neat trimethylborate (10.2 mL, 0.090 mol), and the mixture was allowed to slowly warm to room temperature. The mixture was stirred overnight, then quenched by dropwise addition of 1.0 M aqueous hydrochloric acid. Brine was added, and the organic layer was dried ($Na_2SO_4$) and rotary evaporated. The residue was crystallized from n-heptane to give 4.65 g of crude 4-tert-butyl-phenyl-boronic acid as white needles. This material was used directly in the next reaction without further characterization. Thus, in a manner similar to Example 12, Step (b), 4-tert-butyl-phenyl-boronic acid (0.4287 g, 0.00241 mol) was allowed to react with 4-(4-bromo-phenyl)-4-oxo-butyric acid, methyl ester (0.5443 g, 0.00200 mol) in the presence of tetrakis(triphenylphosphine)palladium(0) (0.0472 g, 0.0000408 mol) and 2.0 M aqueous sodium carbonate (2.4 mL, 0.0048 mol) in toluene (5 mL) to give, after chromatography on silica gel (270 g, 230–400 mesh), eluting with toluene then chloroform, 0.50 g. The material was dissolved in diethyl ether, washed with 0.10 M aqueous sodium hydroxide, water and brine. The organics were dried ($K_2CO_3$), and rotary evaporated to give 0.45 g of 4-(4'-tert-butyl-biphenyl-4-yl)-4-oxo-butyric acid, methyl ester as a white solid; mp 58–62° C.

Step (b) Preparation of 4-(4'-tert-Butyl-biphenyl-4-yl)-4-oxo-butyric acid

In a manner similar to Example 17, Step (b), 4-(4'-tert-butyl-biphenyl-4-yl)-4-oxo-butyric acid, methyl ester (0.43 g, 0.0013 mol) was allowed to react with 1.0 M aqueous sodium hydroxide (2.0 mL, 0.002 mol) in THF-methanol (5 mL each) to give 0.308 g of 4-(4'-tert-butyl-biphenyl-4-yl)-4-oxo-butyric acid as a white solid; mp 172.0–173.5° C.

Step (c) Preparation of 4-(4'-tert-Butyl-biphenyl-4-yl)-4-hydroxyimino-butyric acid In a manner similar to Example 4, Step (c), 4-(4'-tert-butyl-biphenyl-4-yl)-4-oxo-butyric acid (0.277 g, 0.000892 mol) was allowed to react with hydroxylamine hydrochloride (0.0704 g, 0.00101 mol) in the presence of sodium carbonate (0.1074 g, 0.00101 mol) in absolute ethanol (7 mL) to give 0.272 g of 4-(4'-tert-butyl-biphenyl-4-yl)-4-hydroxyimino-butyric acid as a white solid; mp 170.5–171.5° C.

EXAMPLE 24

4-(3',4'-Dichloro-biphenyl-4-yl)-4-hydroxyimino-butyric acid

Step (a) Preparation of 4-(3',4'-Dichloro-biphenyl-4-yl)-4-oxo-butyric acid, methyl ester In a manner similar to Example 12, Step (b), (3,4-dichloro-phenyl)boronic acid (1.0569 g, 0.005539 mol) was allowed to react with 4-(4-bromo-phenyl)-4-oxo-butyric acid, methyl ester (1.3636 g, 0.005019 mol) in the presence of tetrakis(triphenylphosphine(palladium(0) (0.1054 g, 0.0000912 mol) and 2.0 M aqueous sodium carbonate (5.5 mL, 0.011 mol) in toluene (11 mL) to give, after chromatography on silica gel (270 g, 230–400 mesh), eluting with hexanes-acetone (7:1) 1.432 g of 4-(3',4'-dichloro-biphenyl-4-yl)-4-oxo-butyric acid, methyl ester as a white solid: mp 120–121° C.

Step (b) Preparation of 4-(3',4'-Dichloro-biphenyl-4-yl)-4-oxo-butyric acid

In a manner similar to Example 4, Step (b), 4-(3',4'-dichloro-biphenyl-4-yl)-4-oxo-butyric acid, methyl ester (1.360 g, 0.004033 mol) was refluxed in 6 M aqueous hydrochloric acid (25 mL) to give 1.280 g of 4-(3',4'-dichloro-biphenyl-4-yl)-4-oxo-butyric acid as a white solid; mp 154–156° C.

Step (c) Preparation of 4-(3',4'-Dichloro-biphenyl-4-yl)-4-hydroxyimino-butyric acid In a manner similar to Example 4, Step (c), 4-(3',4'-dichloro-biphenyl-4-yl)-4-oxo-butyric acid (1.23 g, 0.00381 mol) was allowed to react with hydroxylamine hydrochloride (0.2994 g, 0.00431 mol) in the presence of sodium carbonate (0.4567 g, 0.00431 mol) in absolute ethanol (20 mL) to give 1.257 g of 4-(3',4'-dichloro-biphenyl-4-yl)-4-hydroxyimino-butyric acid as a white solid; mp 165.5–166.5° C.

What is claimed is:
1. A compound of Formula II

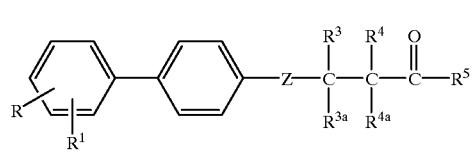

wherein R and $R^1$ are the same or different and are
hydrogen,
alkyl,
halogen,
nitro,
cyano,
trifluoromethyl,
$OCF_3$,
$OCF_2H$, OCH₂F,
—OR⁶ wherein R⁶ is hydrogen,
   alkyl,
   aryl,
   arylalkyl,
   heteroaryl, or
   cycloalkyl,

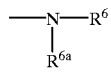

wherein R⁶ and R⁶ᵃ are the same or different and are as defined above for R⁶,

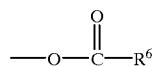

wherein R⁶ is as defined above,

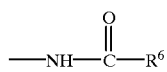

wherein R⁶ is as defined above,

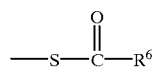

wherein R⁶ is as defined above,
wherein R⁶ is as defined above,

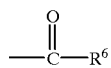

wherein R⁶ is as defined above,
   —CH₂—OR⁶
wherein R⁶ is as defined above,

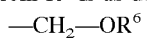

wherein R⁶ and R⁶ᵃ are the same or different and are as defined above for R⁶,

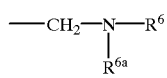

wherein R⁶ and R⁶ᵃ are the same or different and are as defined above for R⁶,

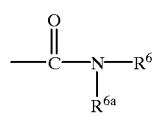

wherein R⁶ is as defined above,

wherein R⁶ is as defined above,

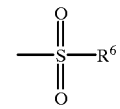

wherein R⁶ is as defined above,
   cycloalkyl, or
   heteroaryl;

Z is 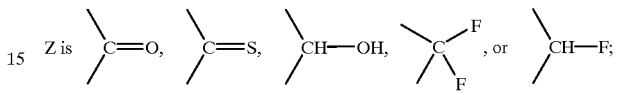

R³, R³ᵃ, R⁴, and R⁴ᵃ are the same or different and are
   hydrogen,
   fluorine,
   alkyl,
   —(CH₂)ₙ-aryl wherein n is an integer from 1 to 6,
   —(CH₂)ₙ-heteroaryl wherein n is as defined above,
   —(CH₂)ₙ-cycloalkyl wherein n is as defined above,
   —(CH₂)ₚ—X—(CH₂)_q-aryl wherein X is O, S, SO, SO₂, or NH, and p and q are each zero or an integer of 1 to 6, and the sum of p+q is not greater than six,
   —(CH₂)ₚ—X—(CH₂)_q-heteroaryl wherein X, p and q are as defined above, or
   —(CH₂)ₙ—R⁷ wherein R⁷ is
      N-phthalimido,
      N-2,3-naphthylimido,
      —OR⁶ wherein R⁶ is as defined above,

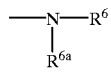

wherein R⁶ and R⁶ᵃ are the same or different and are as defined above for R⁶,

—SR⁶ wherein R⁶ is as defined above,

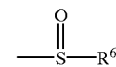

wherein R⁶ is as defined above,

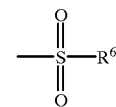

wherein R⁶ is as defined above,

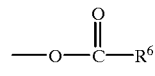

wherein R⁶ is as defined above,

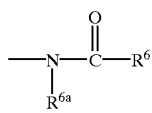

wherein $R^6$ and $R^{6a}$ are the same or different and are as defined above for $R^6$,

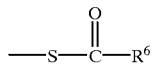

wherein $R^6$ is as defined above,

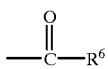

wherein $R^6$ is as defined above, or

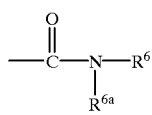

wherein $R^6$ and $R^{6a}$ are the same or different and are as defined above for $R^6$, and
n is as defined above;
$R^5$ is OH, SH, or $OR^{5a}$ wherein $R^{5a}$ is alkyl, arylalkyl, cycloalkyl, or acyloxymethyl; with the proviso that at least one of $R^3$, $R^{3a}$, $R^4$, or $R^{4a}$ is fluorine; or corresponding isomers thereof; or a pharmaceutically acceptable salt thereof.

2. A compound according to claim 1 wherein Z is

and
$R^3$ and $R^{3a}$ are fluorine.

3. A compound according to claim 1 wherein Z is

and
$R^4$ and $R^{4a}$ are fluorine.

4. A compound according to claim 1 wherein Z is

and
$R^3$ is fluorine.

5. A compound according to claim 1 wherein Z is

and
$R^4$ is fluorine.

6. A compound according to claim 1 wherein

Z is 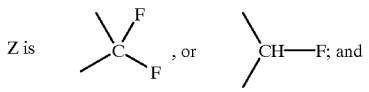

$R^3$ and $R^{3a}$ are fluorine.

7. A compound according to claim 1 wherein

Z is 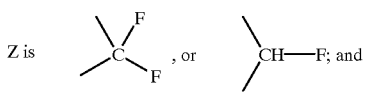

$R^4$ and $R^{4a}$ is fluorine.

8. A compound according to claim 1 wherein

Z is 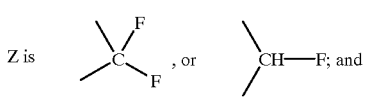

$R^3$ is fluorine.

9. A compound according to claim 1 wherein

Z is 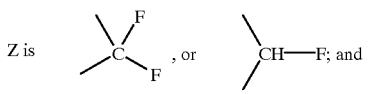

$R^4$ is fluorine.

10. (±)-4-(4'-Chlorobiphenyl-4-yl)-3-fluoro-oxo-butyric acid.

11. A method of inhibiting a matrix metalloproteinase comprising administering to a host suffering therefrom a therapeutically effective amount of a compound according to claim 1 in unit dosage form.

12. A method of inhibiting gelatinase A comprising administering to a host suffering therefrom a therapeutically effective amount of a compound according to claim 11 in unit dosage form.

13. A method of inhibiting stromelysin-1 comprising administering to a host suffering therefrom a therapeutically effective amount of a compound according to claim 1 in unit dosage form.

14. A method of preventing atherosclerotic plaque rupture comprising administering to a host suffering therefrom a therapeutically effective amount of a compound according to claim 1 in unit dosage form.

15. A method of inhibiting aortic aneurism comprising administeringn to a host suffering therefrom a therapeutically effective amount of a compound according to claim 1 in unit dosage form.

16. A method of inhibiting heart failure comprising administering to a host suffering therefrom a therapeutically effective amount of a compound according to claim 1 in unit dosage form.

17. A method of preventing restenosis comprising administering to a host suffering therefrom a therapeutically effective amount of a compound according to claim 1 in unit dosage form.

18. A method of controlling periodontal disease comprising administering to a host suffering therefrom a therapeutically effective amount of a compound according to claim 1 in unit dosage form.

19. A method of treating corneal ulceration comprising administering to a host suffering therefrom a therapeutically effective amount of a compound according to claim 1 in unit dosage form.

20. A method of treating burns comprising administering to a host suffering therefrom a therapeutically effective amount of a compound according to claim 1 in unit dosage form.

21. A method of treating decubital ulcers comprising administering to a host suffering therefrom a therapeutically effective amount of a compound according to claim 1 in unit dosage form.

22. A method of treatment for healing wounds comprising administering to a host suffering therefrom a therapeutically effective amount of a compound according to claim 1 in unit dosage form.

23. A method of treating cancer comprising administering to a host suffering therefrom a therapeutically effective amount of a compound according to claim 1 in unit dosage form.

24. A method of treating arthritis comprising administering to a host suffering therefrom a therapeutically effective amount of a compound according to claim 1 in unit dosage form.

25. A method of treating autoimmune or inflammatory disorders dependent upon tissue invasion by leukocytes comprising administering to a host suffering therefrom a therapeutically effective amount of a compound according to claim 1 in unit dosage form.

26. A method of treating multiple sclerosis comprising administering to a host suffering therefrom a therapeutically effective amount of a compound according to claim 1 in unit dosage form.

27. A method of treating inflammation and pain comprising administering to a host suffering therefrom a therapeutically effective amount of a compound according to claim 1 in unit dosage form.

28. A method of treating acute and chronic neurodegenerative disorders selected from the group consisting of: stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy comprising administering to a host suffering therefrom a therapeutically effective amount of a compound according to claim 1 in unit dosage form.

29. A pharmaceutical composition comprising a compound according to claim 1 in admixture with a pharmaceutically acceptable excipient, diluent, or carrier.

30. A pharmaceutical composition comprising a therapeutically effective amount of a compound according to claim 1 in admixture with a pharmaceutically acceptable excipient, diluent, or carrier.

* * * * *

UNITED STATES PATENT AND TRADEMARK OFFICE
CERTIFICATE OF CORRECTION

PATENT NO. : 6,307,089 B2
DATED : October 23, 2001
INVENTOR(S) : Purchase, Jr. et al.

It is certified that error appears in the above-identified patent and that said Letters Patent is hereby corrected as shown below:

<u>Column 76,</u>
Line 51, "claim 11" should read -- claim 1 --

Signed and Sealed this

Twenty-eighth Day of May, 2002

Attest:

JAMES E. ROGAN
*Attesting Officer*   *Director of the United States Patent and Trademark Office*